United States Patent [19]

Goeddel et al.

[11] Patent Number: 4,929,554

[45] Date of Patent: * May 29, 1990

[54] HUMAN IMMUNE INTERFERON

[76] Inventors: David V. Goeddel, 1449 Benito, Burlingame, Calif. 94010; Patrick W. Gray, 1836 16th Ave., San Francisco, Calif. 94122

[*] Notice: The portion of the term of this patent subsequent to Aug. 9, 2005 has been disclaimed.

[21] Appl. No.: 94,477

[22] Filed: Sep. 4, 1987

Related U.S. Application Data

[63] Continuation of Ser. No. 746,813, Jun. 20, 1985, Pat. No. 4,762,791, which is a continuation of Ser. No. 312,489, Oct. 19, 1981, abandoned.

[51] Int. Cl.$^5$ .................... C12N 15/00; C12N 5/00; C12N 1/20; C12P 21/00; C12P 21/02; C07H 21/04
[52] U.S. Cl. .................. 435/172.3; 435/320; 435/811; 435/240.1; 435/252.3; 435/69.51; 536/27; 935/11; 935/23

[58] Field of Search ............... 435/68, 70, 71, 91, 435/172.1, 172.3, 243, 255, 256, 240.1, 240.2, 811, 320, 252.3, 252.31–252.35; 536/27; 935/11, 27, 28, 23, 29, 68–75, 60

[56] References Cited

U.S. PATENT DOCUMENTS 4,762,791 8/1988 Goeddel et al. ............... 435/243

OTHER PUBLICATIONS

Goeddel et al.; Nature 287: 411 (1980).

Primary Examiner—James Martinell

[57] ABSTRACT

Disclosed is a complete description of the preparation of novel, recombinant human immune interferon and des-CYS-TYR-CYS recombinant human immune interferon via recombinant DNA techniques utilizing any of an assortment of expression vectors and host cultures. The human immune (gamma) interferon (IFN-γ), is isolated and characterized in terms of DNA and amino acid sequences, physical attributes and biological activity.

2 Claims, 15 Drawing Sheets

INDUCED $^{32}$P-cDNA Probe

← H12

UNINDUCED $^{32}$P-cDNA Probe

← H12

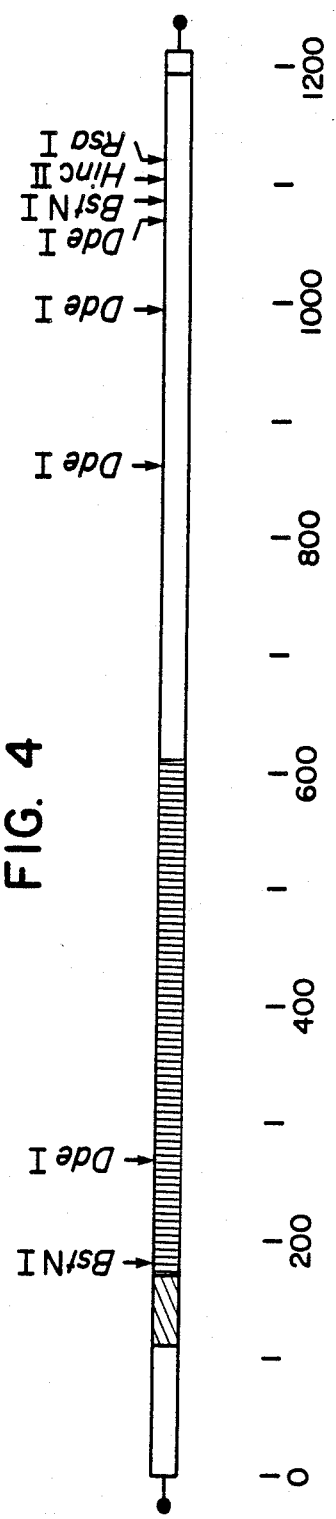
FIG. 4
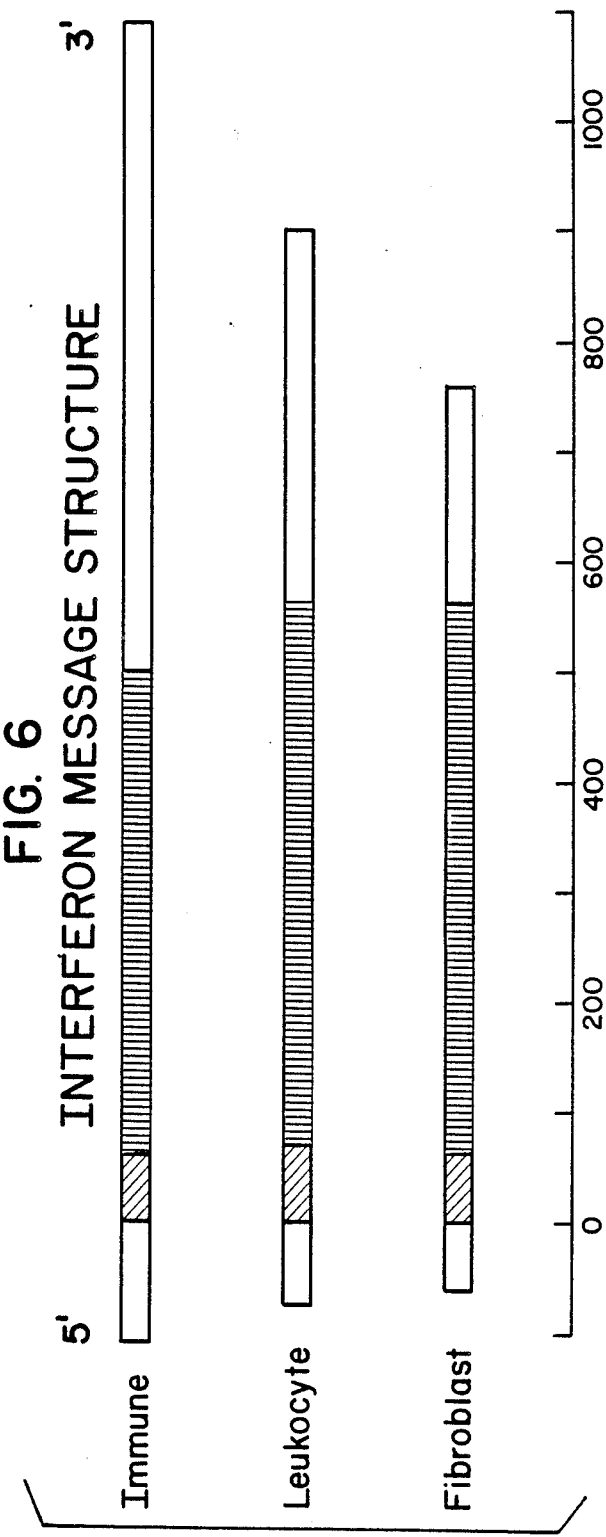
FIG. 6 INTERFERON MESSAGE STRUCTURE

FIG. 5-1

```
5'
TGAAGATCAGCTATTAGAAGAGAAAGATCAGTTAAGTCCTTTGGACCTGATCAGCTGATACAAGAACTACTGATTCAACTTCTTTGGCTTAATTCTCTCGGAAACG ATG AAA TAT
                                                                                                    met lys tyr
                                                                                                    s1
                                                          50                                  100
                                                                                                              10
    thr ser tyr ile leu ala phe gln leu cys ile val leu gly ser leu gly ser leu    cys tyr cys gln asp pro tyr val lys glu ala glu asn
    ACA AGT TAT ATC CTT GCT TTT CAG CTC TGC ATC GTT TTG GGT TCT CTT    TGT TAC TGC CAG GAC CCA TAT GTA AAA GAA GCA GAA AAC
        s10                                                      s20  1                                          200
                                                 150                              30 leu lys tyr phe asn gly ala gly his ser asp val ala asp asn gly thr leu phe leu gly ile leu lys asn trp lys glu glu ser
    CTT AAG TAT TTT AAT GCA GGT CAT TCA GAT GTA GCG GAT AAT GGA ACT CTT TTA GGC ATT TTG AAG AAT TGG AAA GAG GAG AGT
                 20                                      250                                              40 asp arg lys ile met gln ser gln ile val ser phe tyr phe lys asn asp phe lys asn asp phe lys asp asp phe glu lys ser ile gln ser ile lys ser val
    GAC AGA AAA ATA ATG CAG AGC CAA ATT GTC TCC TTT TAC TTC AAA CTT TTT AAA AAC AAC GAT GAC CAG AGC ATC CAA AAG AGT GTG
                            300                                           350                                   450
        50                                                  60                                       70 glu thr ile lys glu asp met asn val lys phe phe asn ser asn lys lys arg asp asp phe glu lys leu thr asn tyr ser val
    GAG ACC ATC AAG GAA GAC ATG AAT GTC AAG TTT TTC AAT AGC AAC AAG AAA CGA GAT GAC TTC GAA AAG CTG ACT AAT TAT TCG GTA
                     400                                                              450
        80                                  90                                              100 thr asp leu asn val gln arg lys ala ile his glu leu ile gln val met ala glu leu ser pro ala ala lys thr gly lys arg lys
    ACT GAC TTG AAT GTC CAA CGC AAA GCA ATA CAT GAA CTC ATC CAA GTG ATG GCT GAA CTG TCG CCA GCA GCT AAA ACA GGG AAG CGA AAA
                                500                                                          550
        110                                          120                                              130
```

```
        140                                        146 STOP
ARG SER GLN MET LEU PHE ARG GLY ARG ARG ALA SER GLN
AGG AGT CAG ATG CTG TTT CGA GGT CGA AGA GCA TCC CAG TAA TGGTTGTCCTGCCTGCAATATTGAATTTAAATCTAAATCTATTAATATTTAACATTA
                                            600                                                   650

TTTATATGGGGAATATATATTTTTAGACTCATCAATCAAATAAGTATTTATAATAGCAACTTTTGTGTAATGAAAATGAATATCTATTAATATGTATATTTATAATTCCTATATCCTG
                         700                                         750

TGACTGTCTCACTTAATCCTTTGTTTCTGACTAATTAGGCAAGGCTATGTGATTACAAGGCTTTATCTCAGGGGCCAACTAGGCAGCAACCTAAGCAAGATCCATGGTTGTGTGTT
                800                                         850                                         900

TATTTCACTTGATGATACAATGAACACTTATAAGTGAAGTGATACTATCCAGTTACTGCCGGTTGAAAATATGCCTGCAATCTGAGCCAGTGCTTTAATGGCATGTCAGACAGAACTT
                         950                                         1000

GAATGTGTCAGGTGACCCTGATGAAAACATAGCATCTCAGGAGATTTCATGCCTGGTGCTTCCAAATATTGTTGACAACTGTGACTGTACCCAAATGGAAAGTAACTCATTGTTAAAA
                1050                                         1100

TTATCAATATCTAATATATGAATAAAGTGTAAGTTCACAACTAAAAAAAAAAAAAAAA
1150                                       1200

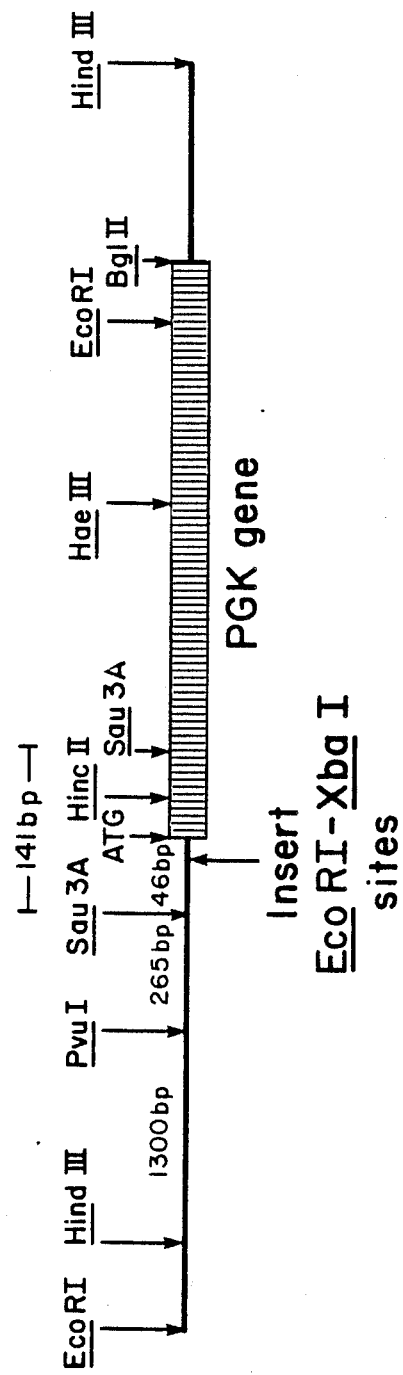

… # HUMAN IMMUNE INTERFERON

This application is a continuing application of application Ser. No. 06/746,813, filed June 20, 1985, now U.S. Pat. No. 4,762,791, which is a continuation of application Ser. No. 06/312,489, filed Oct. 9, 1981, now abandoned.

FIELD OF THE INVENTION

The present invention relates to the field of recombinant DNA technology, to means and methods utilizing such technology in the discovery of the DNA sequence and deduced amino acid sequence for human immune interferon and to its production and to the various products of such production and their uses.

More particularly, the present invention relates to the isolation and identification of DNA sequences encoding human immune interferon and to the construction of recombinant DNA expression vehicles containing such DNA sequences operably linked to expression-effecting promoter sequences and to the expression vehicles so constructed. In another aspect, the present invention relates to host culture systems, such as various microorganism and vertebrate cell cultures transformed with such expression vehicles and thus directed in the expression of the DNA sequences referred to above. In yet other aspects, this invention relates to the means and methods of converting the end products of such expression to novel entities, such as pharmaceutical compositions, useful for the prophylactic or therapeutic treatment of humans. In preferred embodiments, this invention provides particular expression vehicles that are sequenced properly such that human immune interferon is produced and secreted from the host cell in mature form. In addition, this invention relates to various processes useful for producing said DNA sequences, expression vehicles, host culture systems and end products and entities thereof and to specific and associated embodiments thereof.

The present invention arises in part from the discovery of the DNA sequence and deduced amino acid sequence encoding human immune interferon. In addition, the present invention provides sequence information on the 3'- and 5'- flanking sequences of the human immune interferon gene, facilitating the in vitro linkage thereof into expression vehicles. In particular, there is provided the 5'-DNA segment encoding the putative endogenous signal polypeptide which immediately precedes the amino acid sequence of the putative mature human immune interferon. These discoveries, in turn, have enabled the development of the means and methods for producing, via recombinant DNA technology, sufficient amounts of human immune interferon, so as to enable, in turn, the determination of its biochemical properties and bioactivity.

The publications and other materials hereof used to illuminate the background of the invention, and in particular cases, to provide additional details respecting its practice are incorporated herein by reference, and for convenience, are numerically referenced by the following text and respectively grouped in the appended bibliography.

BACKGROUND OF THE INVENTION

A. Human Immune Interferon

Human interferons can be classified in three groups on the basis of different antigenicity and biological and biochemical properties.

The first group comprises a family of leukocyte interferons ($\alpha$-interferon, LeIF or IFN-$\gamma$), which are normally produced mainly by constituent cells of human blood upon viral induction. These have been microbially produced and found to be biologically active (1, 2, 3). Their biological properties have prompted their use in the clinic as therapeutic agents for the treatment of viral infections and malignant conditions (4).

In the second group is human fibroblast interferon ($\beta$-interferon, FIF or IFN-$\beta$), normally produced by fibroblasts upon viral induction, which has likewise been microbially produced and found to exhibit a wide range of biological activities (5). Clinical trials also indicate its potential therapeutic value. The leukocyte and fibroblast interferons exhibit very clear similarities in their biological properties despite the fact that the degree of homology at the amino acid level is relatively low. In addition, both groups of interferons contain from 165 to 166 amino acids and are acid stable proteins.

The human immune interferon ($\gamma$-interferon, IIF or IFN-$\gamma$), to which this invention is directed, is, in contrast to the $\alpha$-and $\beta$-interferons, pH 2 labile, is produced mainly upon mitogenic induction of lymphocytes and is also clearly antigenically distinct. Until recently human immune interferon could only be detected in very minor levels, which evidently hampered its characterization. Recently, rather extensive but still partial purification of human immune interferon has been reported (6). The compound was said to be produced from lymphocyte cultures stimulated with a combination of phytohaemagglutin and a phorbol ester and purified by sequential chromatographic separations. This procedure resulted in a product having a molecular weight of 58,000.

Human immune interferon has been produced in very low amounts by translating mRNA in oocytes, showing interferon activity characteristic of human immune interferon and expressing the hope that immune interferon cDNA could be synthesized and cloned (7).

The amount of immune interferon obtained until now is certainly insufficient to carry out unambiguous experiments on the characterization and biological properties of the purified component. However, in vitro studies performed with crude preparations, as well as in vivo experiments with murine $\gamma$-interferon preparations, suggest that the primary function of immune interferon may be as an immunoregulatory agent (8, 9). Immune interferon has not only an antiviral and anticellular activity in common to all human interferons, but shows a potentiating effect on these activities with $\alpha$- and $\beta$-interferon (10). Also, the in vitro antiproliferative effect of $\gamma$-interferon on tumor cells is reported to be approximately 10- to 100-fold that of the other interferon classes (8, 11, 12). This result, together with its pronounced immunoregulatory role (8, 9), suggests a much more pronounced antitumoral potency for IFN-$\gamma$ than for IFN-$\alpha$ and IFN-$\beta$. Indeed, in vivo experiments with mice and murine IFN-$\gamma$ preparations show a clear superiority over antivirally induced interferons in its antitumoral effect against osteogenic sarcoma (13).

All of these studies, until the present invention, had to be performed with rather crude preparations, due to the very low availability. However, they certainly suggest very important biological functions for immune interferon. Not only has immune interferon a potent associated antiviral activity, but probably also a strong immunoregulatory and antitumoral activity, clearly pointing to a potentially very promising clinical candidate.

It was perceived that the application of recombinant DNA technology would be a most effective way of providing the requisite larger quantities of human immune interferon. Whether or not the materials so produced would include glycosylation which is considered characteristic of native, human derived material, they would probably exhibit bioactivity admitting of their use clinically in the treatment of a wide range of viral, neoplastic, and immunosuppressed conditions or diseases.

B. Recombinant DNA Technology

Recombinant DNA technology has reached the age of some sophistication. Molecular biologists are able to recombine various DNA sequences with some facility, creating new DNA entities capable of producing copious amounts of exogenous protein product in transformed microbes. The general means and methods are in hand for the in vitro ligation of various blunt ended or "sticky" ended fragments of DNA, producing potent expression vehicles useful in transforming particular organisms, thus directing their efficient synthesis of desired exogenous product. However, on an individual product basis, the pathway remains somewhat tortuous and the science has not advanced to a stage where regular predictions of success can be made. Indeed, those who portend successful results without the underlying experimental basis, do so with considerable risk of inoperability.

The plasmid, a nonchromosomal loop of double-stranded DNA found in bacteria and other microbes, oftentimes in multiple copies per cell, remains a basic element of recombinant DNA technology. Included in the information encoded in the plasmid DNA is that required to reproduce the plasmid in daughter cells (i.e., an origin of replication) and ordinarily, one or more phenotypic selection characteristics such as, in the case of bacteria, resistance to antibiotics, which permit clones of the host cell containing the plasmid of interest to be recognized and preferentially grown in selective media. The utility of plasmids lies in the fact that they can be specifically cleaved by one or another restriction endonuclease or "restriction enzyme", each of which recognizes a different site on the plasmid DNA. Thereafter heterologous genes or gene fragments may be inserted into the plasmid by endwise joining at the cleavage site or at reconstructed ends adjacent to the cleavage site. Thus formed are so-called replicable expression vehicles. DNA recombination is performed outside the cell, but the resulting "recombinant" replicable expression vehicle, or plasmid, can be introduced into cells by a process known as transformation and large quantities of the recombinant vehicle obtained by growing the transformant. Moreover, where the gene is properly inserted with reference to portions of the plasmid which govern the transcription and translation of the encoded DNA message, the resulting expression vehicle can be used to actually produce the polypeptide sequence for which the inserted gene codes, a process referred to as expression.

Expression is initiated in a region known as the promoter which is recognized by and bound by RNA polymerase. In the transcription phase of expression, the DNA unwinds, exposing it as a template for initiated synthesis of messenger RNA from the DNA sequence. The messenger RNA is, in turn, translated into a polypeptide having the amino acid sequence encoded by the mRNA. Each amino acid is encoded by a nucleotide triplet or "codon" which collectively make up the "structural gene", i.e. that part which encodes the amino acid sequence of the expressed polypeptide product. Translation is initiated at a "start" signal (ordinarily ATG, which in the resulting messenger RNA becomes AUG). So-called stop codons define the end of translation and, hence, of production of further amino acid units. The resulting product may be obtained by lysing, if necessary, the host cell, in microbial systems, and recovering the product by appropriate purification from other proteins.

In practice, the use of recombinant DNA technology can express entirely heterologous polypeptides—so-called direct expression—or alternatively may express a heterologous polypeptide fused to a portion of the amino acid sequence of a homologous polypeptide. In the latter cases, the intended bioactive product is sometimes rendered bioinactive within the fused, homologous/heterologous polypeptide until it is cleaved in an extracellular environment. See British Patent Publ. No. 2007676A and Wetzel, *American Scientist* 68, 664 (1980).

C. Cell Culture Technology

The art of cell or tissue cultures for studying genetics and cell physiology is well established. Means and methods are in hand for maintaining permanent cell lines, prepared by successive serial transfers from isolate normal cells. For use in research, such cell lines are maintained on a solid support in liquid medium, or by growth in suspension containing support nutriments. Scale-up for large preparations seems to pose only mechanical problems. For further background, attention is directed to *Microbiology*, 2nd Edition, Harper and Row, Publishers, Inc, Hagerstown, Md. (1973) especially pp. 1122 et seq. and *Scientific American* 245, 66 et seq. (1981), each of which is incorporated herein by this reference.

SUMMARY OF THE INVENTION

The present invention is based upon the discovery that recombinant DNA technology can be used to successfully produce human immune interferon, preferably in direct form, and in amounts sufficient to initiate and conduct animal and clinical testing as prerequisites to market approval. The product is suitable for use, in all of its forms, in the prophylactic or therapeutic treatment of human beings for viral infections and malignant and immunosuppressed or immunodeficient conditions. Its forms include various possible oligomeric forms which may include associated glycosylation. The product is produced by genetically engineered transformant microorganisms or transformant cell culture systems. As used herein, the term "transformant cell" refers to a cell into which has been introduced DNA, said DNA arising from exogenous DNA recombination, and to the progeny of any such cell which retains the DNA so introduced. Thus, the potential now exists to prepare and isolate human immune interferon in a more efficient manner than has been possible. One significant factor of the present invention, in its most preferred embodiments, is the accomplishment of genetically directing a microorganism or cell culture to produce human immune interferon in isolatable amounts, secreted from the host cell in mature form.

The present invention comprises the human immune interferon thus produced and the means and methods of its production. The present invention is further directed to replicable DNA expression vehicles harboring gene sequences encoding human immune interferon in expressible form. Further, the present invention is directed to microorganism strains or cell cultures transformed with the expression vehicles described above and to microbial or cell cultures of such transformed strains or cultures, capable of producing human immune interferon. In still further aspects, the present invention is directed to various processes useful for preparing said immune interferon gene sequences, DNA expression vehicles, microorganism strains and cell cultures and to specific embodiments thereof. Still further, this invention is directed to the preparation of fermentation cultures of said microorganisms and cell cultures. In addition, this invention is directed to the preparation of human immune interferon, as a direct expression product, secreted from the host cell in mature form. This approach may utilize the gene encoding the sequence of the mature human immune interferon plus the 5' flanking DNA encoding the signal polypeptide. The signal polypeptide is believed to aid in the transport of the molecule to the cellular wall of the host organisms where it is cleaved during the secretion process of the mature human interferon product. This embodiment enables the isolation and purification of the intended mature immune interferon without resort to involved procedures designed to eliminate contaminants of intracellular host protein or cellular debris.

Reference herein to the expression "mature human immune interferon" connotes the microbial or cell culture production of human immune interferon unaccompanied by the signal peptide or presequence peptide that immediately attends translation of the human immune interferon mRNA. A first recombinant human immune interferon, according to the present invention, is thus provided, having methionine as its first amino acid (present by virtue of the ATG start signal codon insertion in front of the structural gene) or, where the methionine is intra- or extracellularly cleaved, having its normally first amino acid cysteine. Mature human immune interferon can also be produced, in accordance herewith, together with a conjugated protein other than the conventional signal polypeptide, the conjugate being specifically cleavable in an intra- or extracellular environment. See British patent publication No. 2007676A. Finally, the mature human immune interferon can be produced by direct expression without the necessity of cleaving away any extraneous, superfluous polypeptide. This is particularly important where a given host may not, or not efficiently, remove a signal peptide where the expression vehicle is designed to express the mature human interferon together with its signal peptide. The thus produced mature human immune interferon is recovered and purified to a level fitting it for use in the treatment of viral, malignant, and immunosuppressed or immunodeficient conditions.

Human immune interferon was obtained according to the following:

1. Human tissues, for example human spleen tissue or peripheral blood lymphocytes, were cultured with mitogens to stimulate the production of immuned interferon.

2. Cell pellets from such cell cultures were extracted in the presence of ribonuclease inhibitor to isolate all cytoplasmic RNA.

3. An oligo-dT column isolated the total messenger RNA (mRNA) in polyadenylated form. This mRNA was size-fractionated using sucrose density gradient and acid-urea gel electrophoresis.

4. The appropriate mRNA (12 to 18 S) was converted to corresponding single stranded complementary DNA (cDNA) from which was produced double stranded cDNA. After poly-dC tailing, it was inserted into a vector, such as a plasmid bearing one or more phenotypic markers.

5. The thus prepared vectors were used to transform bacterial cells providing a colony library. Radiolabeled cDNA prepared from both induced and uninduced mRNA, derived as described above, was used to separately probe duplicate colony libraries. The excess cDNA was then removed and the colonies exposed to X-ray film so as to identify the induced cDNA clones.

6. From the induced cDNA clones the corresponding plasmid DNA was isolated and sequenced.

7. In a first embodiment sequenced DNA was then tailored in vitro for insertion into an appropriate expression vehicle which was used to transform an *E. coli* host cell which was, in turn, permitted to grow in a culture and to express the desired human immune interferon product.

8. Human immune interferon thus expressed doubtless has 146 amino acids in its mature form, beginning with cysteine, and is very basic in character. Its monomeric molecular weight has been calculated at 17,140. Perhaps because of the presence of numerous basic residues, hydrophobicity, salt bridge formation and so forth, the molecule may associate itself in oligomeric forms, e.g., in dimer, trimer or tetramer form. The high molecular weights previously observed with natural material (6) which can not be accounted for on the basis of the amino acid sequence alone may be due to such oligomeric forms as well as to the contribution of carbohydrate from post-translational glycosylation.

9. In certain host cell systems, particularly when ligated into an expression vehicle so as to be expressed together with its signal peptide, the mature form of human immune interferon is exported into the cell culture medium, immeasurably aiding in recovery and purification methods.

DESCRIPTION OF PREFERRED EMBODIMENTS

A. Microorganisms/Cell Cultures

1. Bacterials Strains/Promoters

The work described herein was performed employing, inter alia, the microorganism *E. coli* K-12 strain 294 (end A, thi−, hsr−, $k$hsm+, as described in British Patent Publication No. 2055382 A. This strain has been deposited with the American Type Culture Collection, ATCC Accession No. 31446. However, various other microbial strains are useful, including known *E. coli* strains such as *E. coli* B, *E. coli* X 1776 (ATCC No. 31537) and *E. coli* W 3110 (F−, x−, protrophic) (ATCC No. 27325), or other microbial strains many of which are deposited and (potentially) available from recognized microorganism depository institutions, such as the American Type Culture Collection (ATCC)—cf. the ATCC catalogue listing. See also German Offenlegungsschrift No. 2644432. These other microorganisms include, for example, Bacilli such as Bacillus subtilis and other enterobacteriaceae among which can be mentioned as examples Salmonella typhimurium and Serratia marcesans, utilizing plasmids that can replicate and express heterologous gene sequences therein.

As examples, the beta lactamase and lactose promoter systems have been advantageously used to initiate and sustain microbial production of heterologous polypeptides. Details relating to the make-up and construction of these promoter systems have been published by Chang et al., Nature 275, 617 (1978) and Itakura et al., Science 198, 1056 (1977), which are hereby incorporated by reference. More recently, a system based upon tryptophan, the so-called trp promoter system, has been developed. Details relating to the make-up and construction of this system have been published by Goeddel et al., Nucleic Acids Research 8, 4057 (1980) and Kleid et al., U.S.S.N. 133, 296, filed Mar. 24, 1980, which are hereby incorporated by reference. Numerous other microbial promoters have been discovered and utilized and details concerning their nucleotide sequences, enabling a skilled worker to ligate them functionally within plasmid vectors, have been published—see, e.g., Siebenlist et al., Cell 20, 269 (1980), which is incorporated herein by this reference.

2. Yeast Strains/Yeast Promoters

The expression system hereof may also employ the plasmid YRp7 (14, 15, 16), which is capable of selection and replication in both E. coli and the yeast, Saccharomyces cerevisiae. For selection in yeast the plasmid contains the TRP1 gene (14, 15, 16) which complements (allows for growth in the absence of tryptophan) yeast containing mutations in this gene found on chromosome IV of yeast (17). The strain used here was the strain RH218 (18) deposited at the American Type Culture Collection without restriction (ATCC No. 44076). However, it will be understood that any Saccharomyces cerevisiae strain containing a mutation which makes the cell trp1 should be an effective environment for expression of the plasmid containing the expression system. An example of another strain which could be used is pep4-1 (19). This tryptophan auxotroph strain also has a point mutation in TRP1 gene.

When placed on the 5' side of a non-yeast gene the 5'-flanking DNA sequence (promoter) from a yeast gene (for alcohol dehydrogenase 1) can promote the expression of a foreign gene in yeast when placed in a plasmid used to transform yeast. Besides a promoter, proper expression of a non-yeast gene in yeast requires a second yeast sequence placed at the 3'-end of the non-yeast gene on the plasmid so as to allow for proper transcription termination and polyadenylation in yeast. This promoter can be suitably employed in the present invention as well as others—see infra. In the preferred embodiments, the 5'-flanking sequence of the yeast 3-phosphoglycerate kinase gene (20) is placed upstream from the structural gene followed again by DNA containing termination - polyadenylation signals, for example, the TRP1 (14, 15, 16) gene or the PGK (20) gene.

Because yeast 5'-flanking sequence (in conjunction with 3' yeast termination DNA) (infra) can function to promote expression of foreign genes in yeast, it seems likely that the 5'-flanking sequences of any highly-expressed yeast gene could be used for the expression of important gene products. Since under some circumstances yeast expressed up to 65 percent of its soluble protein as glycolytic enzymes (21) and since this high level appears to result from the production of high levels of the individual mRNAs (22), it should be possible to use the 5'-flanking sequences of any other glycolytic genes for such expression purposes - e.g., enolase, glyceraldehyde -phosphate dehydrogenase, hexokinase, pyruvate decarboxylase, phosphofructokinase, glucose - 6-phosphate isomerase, 3-phosphoglycerate mutase, pyruvate kinase, triosephosphate isomerase, phosphoglucose isomerase, and glucokinase. Any of the 3'-flanking sequences of these genes could also be used for proper termination and mRNA polyadenylation in such an expression system—cf. Supra. Some other highly expressed genes are those for the acid phosphatases (23) and those that express high levels of production due to mutations in the 5'-flanking regions (mutants that increase expression)—usually due to the presence of a TY1 transposable element (24).

All of the genes mentioned above are thought to be transcribed by yeast RNA polymerase 11 (24). It is possible that the promoters for RNA polymerase I and III which transcribe genes for ribosomal RNA, 5S RNA, and tRNAs (24, 25), may also be useful in such expression constructions.

Finally, many yeast promoters also contain transcriptional control s they may be turned off or on by variation in growth conditions. Some examples of such yeast promoters are the genes that produce the following proteins: Alcohol dehydrogenase II, isocytochrome-c, acid phosphatase, degradative enzymes associated with nitrogen metabolism, glyceraldehyde -3-phosphate dehydrogenase, and enzymes responsible for maltose and 9alactose utilization (22). Such a control region would be very useful in controlling expression of protein product—especially when their production is toxic to yeast. It should also be possible to put the control region of one 5'-flanking sequence with a 5'-flanking sequence containing a promoter from a highly expressed gene. This would result in a hybrid promoter and should be possible since the control region and the promoter appear to be physically distinct DNA sequences.

3. Cell Culture Systems/Cell Culture Vectors

Propogation of vertebrate cells in culture (tissue culture) has become a routine procedure in recent year-s (see Tissue Culture, Academic Press, Kruse and Patterson eds, 1973). Employed herein was the COS-7 line of monkey kidney fibroblasts as the host for the production of immune interferon (25a). However, the experiments detailed here could be performed in any cell line which is capable of the replication and expression of a compatible vector, e.g., W138, BHK, 3T3,.CHO, VERO, and HeLa cell lines. Additionally, what is required of the expression vector is an origin of replication and a promoted located in front of the gene to be expressed, along with any necessary ribosome binding sites, RNA splice sites, polyadenylation site, and transcriptional terminator sequences. While these essential elements of SV40 have been exploited herein, it will be understood that the invention, although described herein in terms of a preferred embodiment, should not be construed as limited to these sequences. For example, the origin of replication of other viral (e.g., Polyoma, Adeno, VSV, BPV, and so forth) vectors could be used, as well as cellular origins of DNA replication which could function in a nonintegrated state.

B. Vector Systems

1. Direct Expression of Mature Immune Interferon in E. coli

The procedure used to obtain direct expression of IFN-γ in *E. coli* as a mature interferon polypeptide (minus. signal sequence) was a variant of that employed earlier for human growth hormone (26) and human leukocyte interferon (1), insofar as it involved the combination of synthetic (N-terminal) and cDNAs.

As deduced from the nucleotide sequence of p69, described infra, and by comparison with the known cleavage site between signal peptide and mature polypeptide for several IFN-αs (2), IFN-γ has a hydrophobic signal peptide of 20 amino acids followed by 146 amino acids of mature IFN-γ (FIG. 5). As shown in FIG. 7, a BstNI restriction endonuclease site is conveniently located at amino acid 4 of mature IFN-γ. Two synthetic oligodeoxynucleotides were designed which incorporate an ATG translational initiation codon, codons for amino acids 1, 2 and 3 (cysteine-tyrosine-cysteine) and create an EcoRI cohesive end. These deoxyoligonucleotides were ligated to a 100 base pair BstNI-PstI fragment of p69 to construct a 1115 base pair synthetic-natural hybrid gene which codes for IFN-γ and which is bounded by EcoRI and PstI restriction sites. This gene was inserted into the plasmid pLeIF A trp 103 between the EcoRI and PstI sites to give the expression plasmid pIFN-γ trp 48. In this plasmid the IFN-γ gene is expressed under the control of the *E. coli* trp promoter. (pLeIF A trp 103 is a derivative of pLeIF A 25 in which the EcoRI site distal to the LeIF A gene was removed. The procedure used to remove this EcoRI site has been described previously (27)).

2. Expression in Yeast

To express a heterologous gene such as the cDNA for immune interferon in yeast, it was necessary to construct a plasmid vector containing four components. The first component is the part which allows for transformation of both *E. coli* and yeast and thus must contain a selectable gene from each organism. (In this case, this is the gene for ampicillin resistance from *E. coli* and the gene TRP1 from yeast.) This component also requires an origin of replication from both organisms to be maintained as a plasmid DNA in both organisms. (In this case, this is the *E. coli* origin from pBR322 and the ars1 origin from chromosome III of yeast.)

The second component of the plasmid is a 5'-flanking sequence from a highly expressed yeast gene to promote transcription of a downstream-placed structural gene. In this case, the 5'-flanking sequence used is that from the yeast 3-phosphoglycerate kinase (PGK) gene. The fragment was constructed in such a way so as to remove the ATG of the PGK structural sequence as well as 8 bp upstream from this ATG. This sequence was replaced with a sequence containing both an XbaI and EcoRI restriction site for convenient attachment of this 5'-flanking sequence to the structural gene.

The third component of the system is a structural gene constructed in such a manner that it contains both an ATG translational start and translational stop signals. The isolation and construction of such a gene is described infra.

The fourth component is a yeast DNA sequence containing the 3'-flanking sequence of a yeast gene, which contains the proper signals for transcription termination and polyadenylation.

With all these components present, immune interferon has been produced in yeast.

3. Expression in Mammalian Cell Culture

The strategy for the synthesis of immune interferon in mammalian cell culture relied on the development of a vector capable of both autonomous replication and expression of a foreign gene under the control of a heterologous transcriptional unit. The replication of this vector in tissue culture was accomplished by providing a DNA replication origin (derived from SV40 virus), and providing helper function (T antigen) by the introduction of the vector into a cell line endogenously expressing this antigen (28, 29). The late promoter of SV40 virus preceded the structural gene of interferon and ensured the transcription of the gene.

The vector used to obtain expression of IFN-γ consisted of pBR322 sequences which provided a selectable marker for selection in *E. coli* (ampicillin resistance) as well as an *E. coli* origin of DNA replication. These sequences were derived from the plasmid pML-1 (28) and encompassed the region spanning the EcoRI and BamHI restriction sites. The SV40 origin is derived from a 342 base pair PvuII-HindIII fragment encompassing this region (30, 31) (both ends being converted to EcoRI ends). These sequences, in addition to comprising the viral origin of DNA replication, encode the promoter for both the early and late transcriptional unit. The orientation of the SV40 origin region was such that the promoter for the late transcriptional unit was positioned proximal to the gene encoding interferon.

BRIEF DESCRIPTION OF THE DRAWINGS

FIG. 4 is a restriction endonuclease map of the clone 69 cDNA insert. The cDNA insert is bounded by PstI sites (dots at both ends) and oligo dC-dG tails (single lines). The number and size of fragments produced by restriction nuclease cleavage was estimated by electrophoresis through 6 percent acrylamide gels. Positions of sites was confirmed by nucleic acid sequencing (presented in FIG. 5). The coding region of the largest open reading frame is boxed and the hatched region represents the putative 20 residue signal peptide sequence, while the stipled region represents the mature IIF sequence (146 amino acids). The 5' end of the mRNA is to the left while the 3' end is to the right.

FIG. 5 illustrates the nucleotide sequence of the plasmid 69 cDNA insert. The deduced amino acid sequence of the longest open reading frame is also presented. The putative signal sequence is represented by the residues labelled S1 to S20.

FIG. 6 is a comparison of IFN-γ mRNA structure with that of leukocyte (IFN-α) and fibroblast (IFN-β) interferons. The clone 69 mRNA (labelled immune) contains significantly greater amounts of untranslated sequences.

FIG. 11 schematically illustrates the restriction map of the 3.1 kbp HindIII insert of vector pB1 from which the PGK promoter was isolated. Indicated is the insertion of an EcoRI site and an XbaI site in the 5'-flanking DNA of the PGK gene.

FIG. 12 illustrates the 5'-flanking sequence plus the initial coding sequence for the PGK gene before insertion of an XbaI and EcoRI sites.

DETAILED DESCRIPTION

A. Source of IFN-γ mRNA

Peripheral Blood Lymphocytes (PBLs) were derived from human donors by leukophoresis. PBLs were further purified by Ficoll-Hypaque gradient centrifugation and then cultured at a concentration of $5 \times 10^6$ cells/ml in RPMI 1640, 1 percent. L-glutamine, 25 mM HEPES, and 1 percent penicillin-streptomycin solution (Gibco, Grand Island, N.Y.). These cells were induced to produce IFN-γ by the mitogen staphlococcal enterotoxin B (1 μg/ml) and cultured for 24 to 48 hours at 37° C. in 5 percent $CO_2$. Desacetylthymosin-α-1 (0.1 μg/ml) was added to PBL cultures to increase the relative yield of IFN-γ activity.

B. Messenger RNA Isolation

Total RNA from PBL cultures wa extracted essentially as reported by Berger, S. L. et al. (33). Cells were pelleted by centrifugation and then resuspended in 10 mM NaCl, 10 mM Tris-HCl (pH 7.5), 1.5 mM $MgCl_2$ and 10 mM ribonucleoside vanadyl complex. Cells were lysed by the addition of NP-40 (1 percent final concentration), and nuclei were pelleted by centrifugation. The supernatant contained the total RNA which was further purified by multiple phenol and chloroform extractions. The aqueous phase was made 0.2 M in NaCl and then total RNA was precipitated by the addition of two volumes of ethanol. RNA from uninduced (non-stimulated) cultures was isolated by the same methods. Oligo-dT cellulose chromatography was utilized to purify mRNA from the total RNA preparations (34). Typical yields from 1–2 liters of cultured PBLs were 5–10 milligrams of total RNA and 50–200 micrograms of Poly(A)+RNA.

C. Size Fractionation of mRNA

Two methods were used to fractionate mRNA preparations. These methods were used independently (rather than in unison) and each resulted in a significant enrichment of IFN-γ mRNA.

Figure 1:
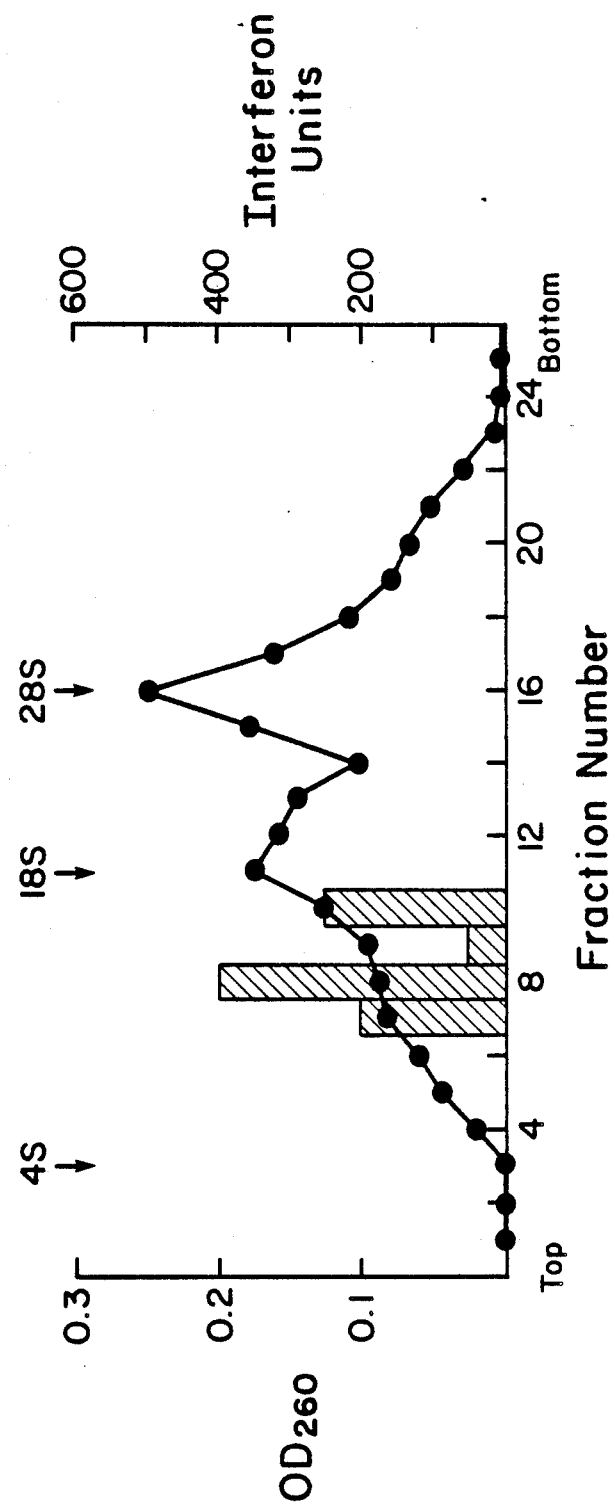
FIG. 1 depicts a sucrose gradient centrifugation of induced Peripheral Blood Lymphocyte (PBL) Poly-(A)+RNA. Two peaks of interferon activity were observed (as shown by the hatched boxes) with sizes of 12S and 16S. The positions of ribosomal RNA markers (centrifuged independently) are labeled above the absorbance profile.

Sucrose gradient centrifugation in the presence of the denaturant formamide was used to fractionate mRNA. Gradients of 5 percent to 25 percent sucrose in 70 percent formamide (32) were centrifuged at 154,000 × g for 19 hours at 20° C. Successive fractions (0.5 ml) were then removed from the top of the gradient, ethanol precipitated, and an aliquot was injected into *Xenopus laevis* oocytes for translation of the mRNA (35). After 24 hrs. at room temperature, the incubation medium was then assayed for antiviral activity in a standard cytopathic effect inhibition assay employing Vesicular Stomatitis Virus (Indiana strain) or Encephalomyocarditis Virus on WISH (human amnion) cells as described by Stewart (36), except that the samples were incubated with the cells for 24 hours (instead of 4) prior to challenge with the virus. Two activity peaks were consistently observed in sucrose gradient fractionated RNA (FIG. 1). One peak sedimented with a calculated size of 12S and contained 100–400 units/ml of antiviral activity (compared with a IFN-α standard) per microgram of RNA injected. The other peak of activity sedimented as 16S in size and contained about half the activity of the slower sedimenting peak. Each of these activity peaks appears to be due to IFN-γ, since no activity was observed when the same fractions were assayed on a bovine cell line (MDBK) which is not protected by human IFN-γ. Both IFN-α activity and IFN-β activity would have been easily detected with the MDBK assay (5).

Figure 2:
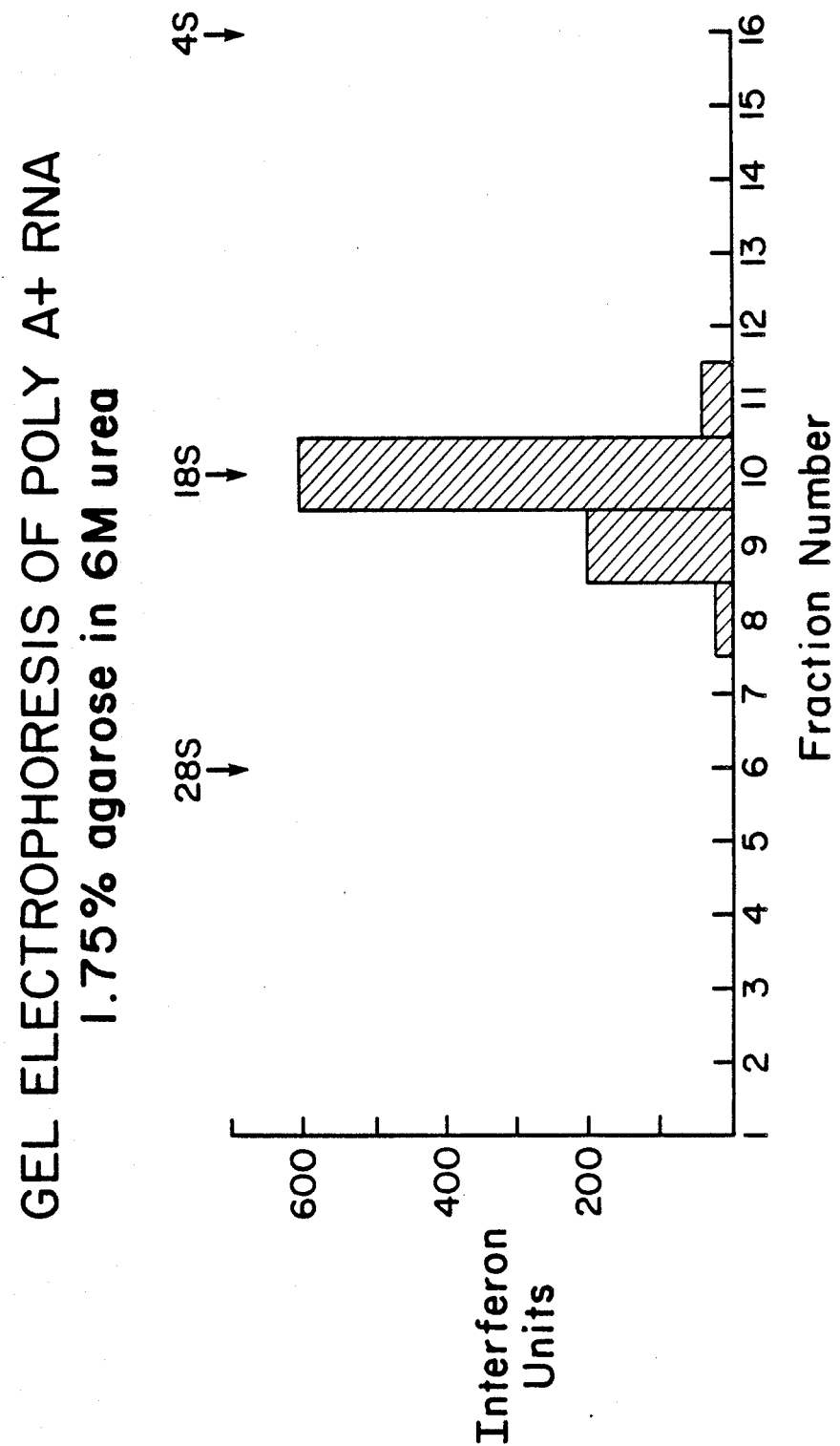
FIG. 2 depicts an electrophoresis of induced PBL Poly(A)+ RNA through an acid-urea-agarose. Only one peak of activity was observed, which comigrated with 18S RNA. The positions of ribosomal RNA markers which were electrophoresed in an adjacent lane and visualized by ethidium bromide staining are labeled above the activity profile.

Fractionation of mRNA (200 vg) was also performed by electrophoresis through acid urea agarose gels. The slab agarose gel (37, 38) was composed of 1.75 percent agarose, 0.025 M sodium citrate, pH 3.8 and 6 M urea. Electrophoresis was performed for 7 hours at 25 milliamp and 4° C. The gel was then fractionated with a razor blade. The individual slices were melted at 70° C. and extracted twice with phenol and once with chloroform. Fractions were then ethanol precipitated and subsequently assayed for IFN-γ mRNA by injection into *Xenopus laevis* oocytes and antiviral assay. Only one peak of activity was observed in gel fractionated samples (FIG. 2). This peak comigrated with 18S RNA and had an activity of 600 units/ml per microgram of injected RNA. This activity also appeared to be IFN-γ specific, since it did not protect MDBK cells.

The size discrepancy between activity peaks observed on sucrose gradients (12S and 16S) and acid urea gels (18S) may be explained by the observation that these independent fractionation methods are not performed under total denaturing conditions.

D. Preparation of a Colony Library Containing IFN-γ Sequences

3 µg of gel-fractionated mRNA was used for the preparation of double stranded cDNA by standard procedures (26, 39). The cDNA was size fractionated on a 6 percent polyacrylamide gel. Two size fractions were electroeluted, 800–1500 bp (138 ng) and >1500 bp (204 ng). 35 ng portions of each size cDNA was extended with deoxyC residues using terminal deoxynucleotidyl transferase (40) and annealed with 300 ng of the plasmid pBR322 (41) which had been similarly tailed with deoxyG residues at the PstI site (40). Each annealed mixture was then transformed into *E. coli* K12 strain 294. Approximately 8000 transformants were obtained with the 800–1500 bp cDNA and 400 transformants were obtained with the >1500 bp cDNA.

E. Screening of Colony Library for Induced cDNAs

The colonies were individually inoculated into wells of microtitre plates containing LB (58) +5 µg/ml tetracycline and stored at −20° C. after addition of DMSO to 7 percent. Two copies of the colony library were grown up on nitrocellulose filters and the DNA from each colony fixed to the filter by the Grunstein-Hogness procedure (42).

Figures 1, 3:
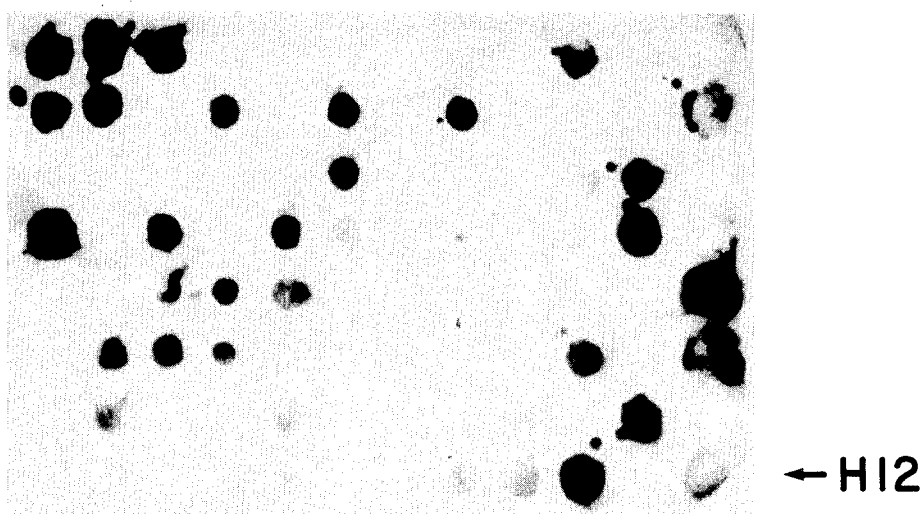
FIG. 3 shows hybridization patterns of 96 colonies with induced and uninduced $^{32}$P-labelled cDNA probes. 96 individual transformants were grown in a microtiter plate, replica plated on two nitrocellulose membranes, and then the filters were hybridized with $^{32}$P-cDNA probes prepared from either induced mRNA (above) or mRNA isolated from uninduced PBL cultures (uninduced, below). The filters were washed to remove non-hybridized RNA and then exposed to X-ray film. This set of filters is representative of 86 such sets (8300 independent colonies). An example of an "induced" clone is labelled as H12.
Figures 2, 3:
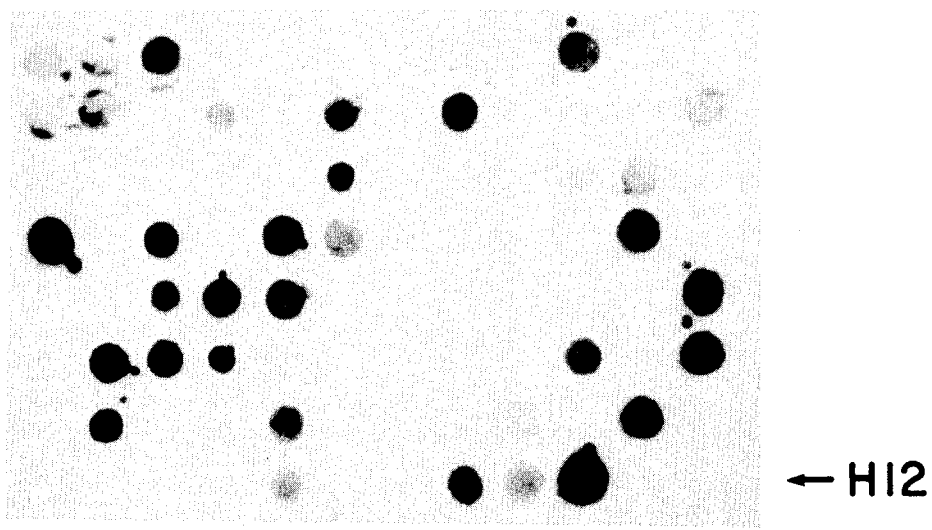

$^{32}$P-labelled cDNA probes were prepared using 18S side gel fractionated mRNA from induced and uninduced PBL cultures. Oligo dT$_{12-18}$ was the primer used and reaction conditions have been previously described (1). Filters containing 8000 transformants from the 600–1500 bp cDNA size cut and 400 transformants from the >1500 bp cDNA size cut were hybridized with 20×10$^6$ cpm of induced $^{32}$P-cDNA. A duplicate set of filters was hybridized with 20×10$^6$ cpm of uninduced $^{32}$P-cDNA. Hybridization was for 16 hours using conditions described by Fritsch et al. (43). Filters were extensively washed (43) and then exposed to Kodak XR-5 X-ray film with DuPont Lightning-Plus intensifying screens for 16–48 hours. Each colony's hybridization pattern with the two probes was compared. Approximately 40 percent of the colonies clearly hybridized with both probes, while approximately 50 percent of the colonies failed to hybridize with either probe (presented in FIG. 3). 124 colonies hybridized significantly with the induced probe but undetectably or more weakly with the uninduced probe. These colonies were individually inoculated into wells of microtitre plates, grown and transferred to nitrocellulose filters, and hybridized with the same two probes, as described above. Plasmid DNA isolated from each of these colonies by a rapid method (44) was also bound to nitrocellulose filters and hybridized (45) with the induced and uninduced probes. DNA from 22 colonies hybridized with only the induced probe and were termed "induced" colonies.

F. Characterization of Induced Colonies

Plasmid DNA was prepared from 5 of the induced colonies (46) and used for characterization of the cDNA inserts. Restriction endonuclease mapping of five induced plasmids (p67, p68, p69, p71 and p72) suggested that four had similar restriction nuclease maps. These four (p67, p69, p71 and p72) each had four DdeI sites, 2 HinfI sites, and a single RsaI site in the cDNA insert. The fifth plasmid (p68) contained a common DdeI fragment and appeared to be a short cDNA clone related to the other four. The homology suggested by restriction nuclease mapping was confirmed by hybridization. A $^{32}$P-labelled DNA probe was prepared (47) from a 600 bp DdeI fragment of the p67 plasmid and used for hybridization (42) to the other induced colonies All five of the restriction nuclease mapped colonies cross-hybridized with this probe, as did 17 other colonies of the 124 chosen in the induced/uninduced screening. The length of cDNA insert in each of these cross-hybridizing plasmids was determined by PstI digestion and gel electrophoresis. The clone with the longest cDNA insert appeared to be clone 69 with an insert length of 1200–1400 bp. This DNA was used for all further experiments, and its restriction endonuclease map is shown in FIG. 4.

The cDNA insert in p69 was demonstrated to be IFN-γ cDNA by its expression products, produced in three independent expression systems, yielding antiviral activity, as described in more detail infra.

G. Sequence Analysis of cDNA Insert of p69

The complete nucleotide sequence of the plasmid p69 cDNA insert was determined by the dideoxynucleotide chain termination method (48) after subcloning fragments into the M13 vector mp7 (49) and by the Maxam-Gilbert chemical procedure (52). The longest open reading frame encodes a protein of 166 amino acids, presented in FIG. 5. The first residue encoded is the first met codon encountered in the 5' end of the cDNA. The first 20 residues at the amino terminus probably serves as a signal sequence for the secretion of the remaining 146 amino acids. This putative signal sequence has features in common with other characterized signal sequences such as size and hydrophobicity. Furthermore, the four amino acids found at the putative cleavage sequence (ser-leu-gly-cys) re identical with four residues found at the cleavage point of several leukocyte interferons (LeIF B, C, D, F, and H, (2)). The encoded mature amino acid sequence of 146 amino acids (hereinafter referred to as "recombinant human immune interferon" has a molecular weight of 17,140.

There are two potential glycosylation positions (50) in the encoded protein sequence, at amino acids 28 to 30 (asn-gly-thr) and amino acids 100 to 102 (asn-tyr-ser). The existence of these positions is consistent with the observed glycosylation of human IFN-γ (6, 51). In addition, the only two cysteine residues (positions 1 and 3) are sterically too close to form a disulfide bridge, which is consistent with the observed stability of IFN-γ in the presence of reducing agents such as β-mercaptoethanol (51). The deduced mature amino acid sequence is generally quite basic, with 30 total lysine, arginine, and histidine residues and only 19 total aspartic acid and glutamic acid residues.

The mRNA structure of IFN-γ as deduced from DNA sequence of plasmid p69 is distinctively different from IFN-α (1, 2) or IFN-β (5) mRNA. As presented in FIG. 6, the coding region of IFN-γ is shorter while the 5' untranslated and 3' untranslated regions are much longer than either IFN-α or IFN-β.

H. Expression of Recombinant Human Immune Interferon in E. coli

Figure 7:
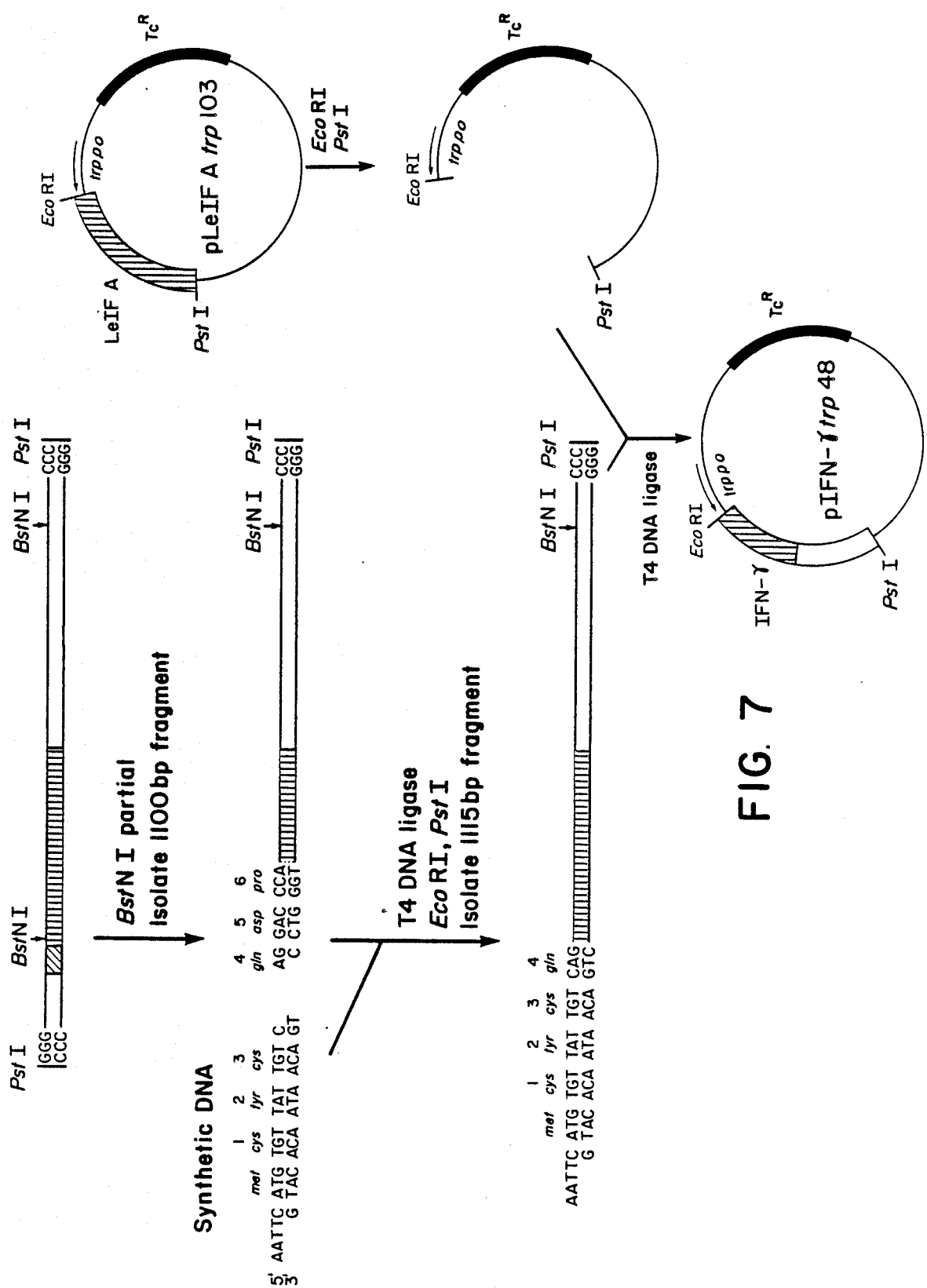
FIG. 7 is a schematic diagram of the construction of the IFN-γ expression plasmid pIFN-γ trp 48. The starting material is the 1250 base pair PstI cDNA insert from plasmid p69.
Figure 8:
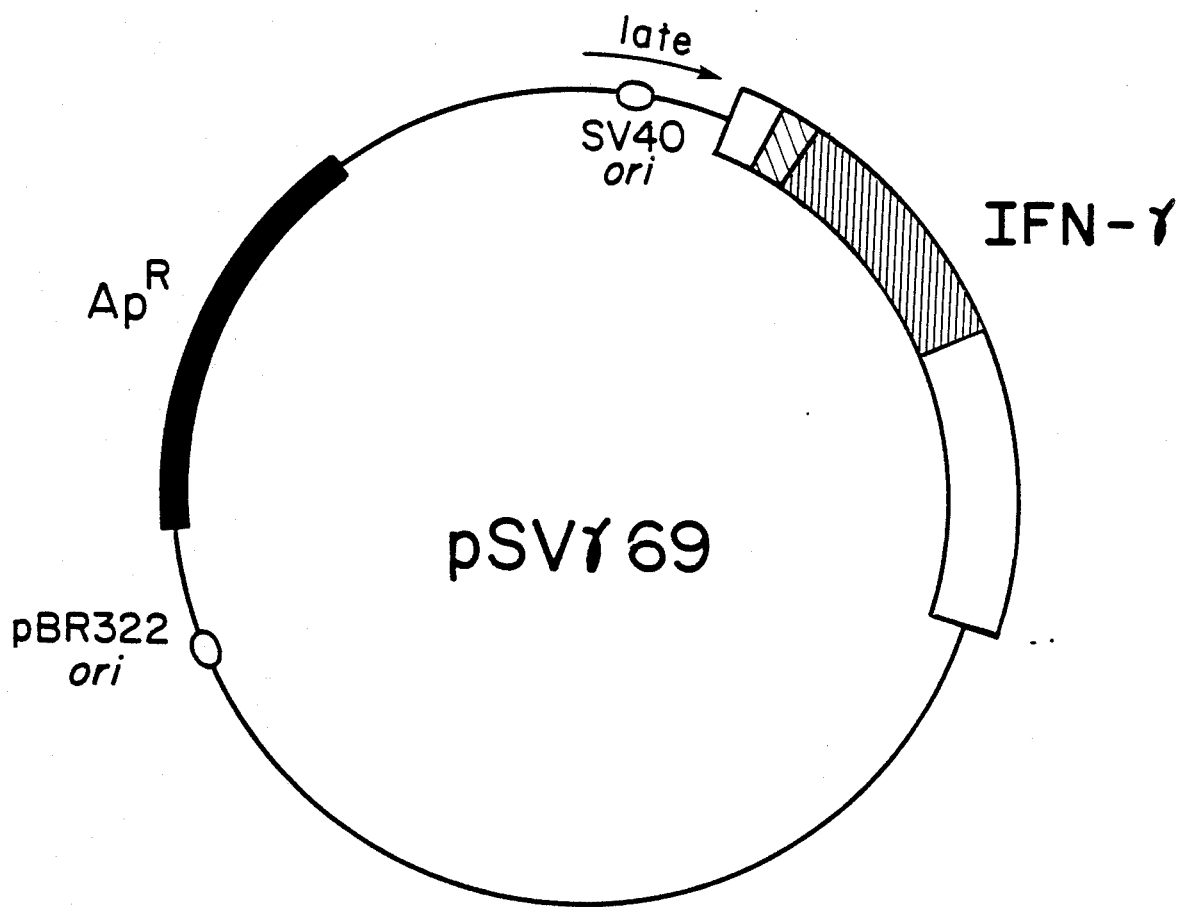
FIG. 8 shows a diagram of plasmid used for expression of IFN-γ in monkey cells.

With reference to FIG. 7, 50 ng of plasmid p69 were digested with PstI and the 1250 base pair insert isolated by gel electrophoresis on a 6 percent polyacrylamide gel. Approximately 10 μg of this insert was electroeluted from the gel. 5 μg of this PstI fragment was partially digested with 3 units of BstNI (Bethesda Research Labs) for 15 minutes at 37° C. and the reaction mixture purified on a 6 percent polyacrylamide gel. Approximately 0.5 μg of the desired 1100 base pair BstNI - PstI fragment was recovered. The two indicated deoxyoligonucleotides, 5'-dAATTCATGTGT-TATTGTC and 5'-dTGACAATAACACATG (FIG. 7) were synthesized by the phosphotriester method (53) and phosphorylated as follows. 100 pmoles of each deoxyoligonucleotide were combined in 30 μl of 60 mM Tris-HCl (pH 8), 10 mM MgCl$_2$, 15 mM βmercaptoethanol and 240 μCi (γ-$^{32}$P)ATP (Amersham, 5000 Ci/mmole). 12 units of T4 polynucleotide kinase were added and the reaction allowed to proceed at 37° C. for 30 minutes. 1 μl of 10 mM ATP was added and the reaction allowed to proceed an additional 20 minutes. After φ-OH/CHCl$_3$ extraction the oligomers were combined with 0.25 μg of the BstNI-PstI 1100 base pair fragment and ethanol precipitated. These fragments were ligated at 20° C. for 2 hours in 30 μl of 20 mM Tris-HCl (pH 7.5), 10 mM MgCl$_2$, 10 mM dithiothreitol, 0.5 mM ATP and 10 units T4 DNA ligase. The mixture was digested for 1 hour with 30 units of PstI and 30 units of EcoRI (to eliminate polymerization through ligation of cohesive termini) and electrophoresed on a 6 percent polyacrylamide gel. The 1115 base pair product (110,000 cpm) was recovered by electroelution.

The plasmid pLeIF A trp 103 (FIG. 7) is a derivative of the plasmid pLeIF A 25 (1) in which the EcoRI site distal to the LeIF A gene has been removed (27). 3 μg of pLeIF A trp 103 was digested with 20 units of EcoRI and 20 units of PstI for 90 minutes at 37° C. and electrophoresed on a 6 percent polyacrylamide gel. The large (~3900 base pair) vector fragment was recovered by electroelution. The 1115 base pair EcoRI-PstI IFN-γ DNA fragment was ligated into 0.15 μg of this prepared vector. Transformation of E. coli K-12 strain 294 (ATCC No. 31446) gave 120 tetracycline resistant colonies. Plasmid DNA was prepared from 60 of these transformants and digested with EcoRI and PstI. Three of these plasmids contained the desired 1115 base pair EcoRI-PstI fragment. DNA sequence analysis verified that these plasmids had the desired nucleotide sequence at the junctions between the trp promoter, synthetic DNA and cDNA. One of these plasmids pIFN-γ trp 48 was chosen for addItional study. This plasmid was used to transform the E. coli K-12 strain W3110 (ATCC No. 27325).

I. Gene Structure of the IFN-γ Coding Sequence

Figure 9:
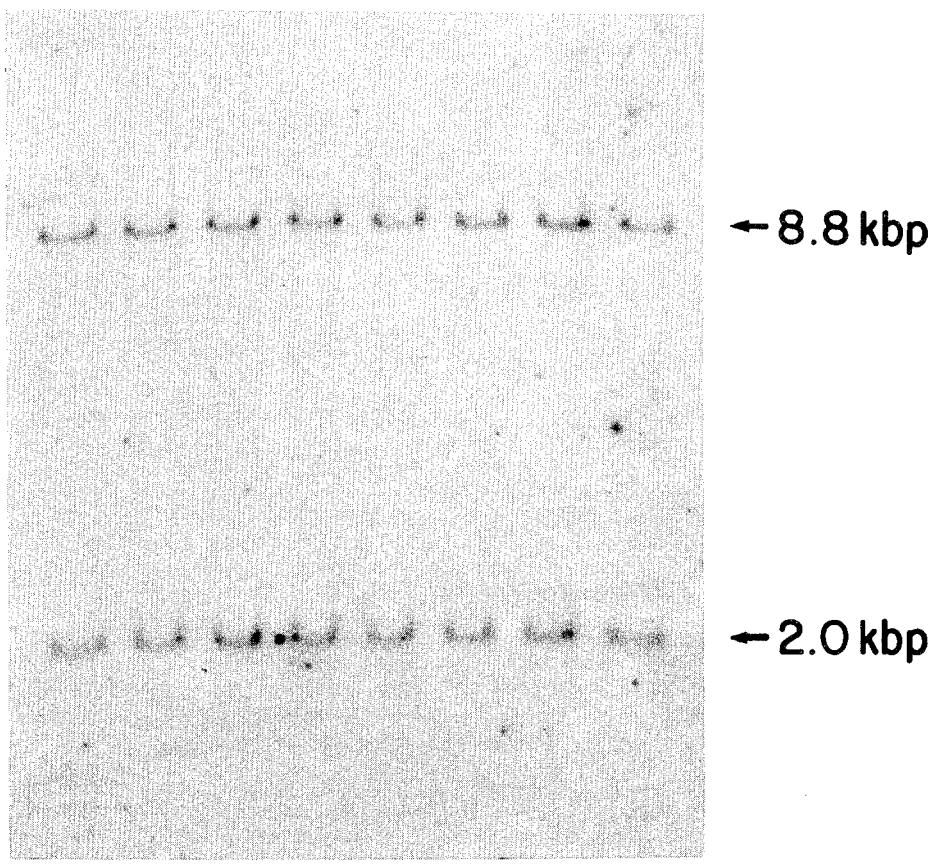
FIG. 9 depicts a Southern hybridization of eight different EcoRI digested human genomic DNAs hybridized with a $^{32}$P-labelled 600 base pair DdeI fragment from the cDNA insert of p69. Two EcoRI fragments clearly hybridize with the probe in each DNA sample.
Figure 10:
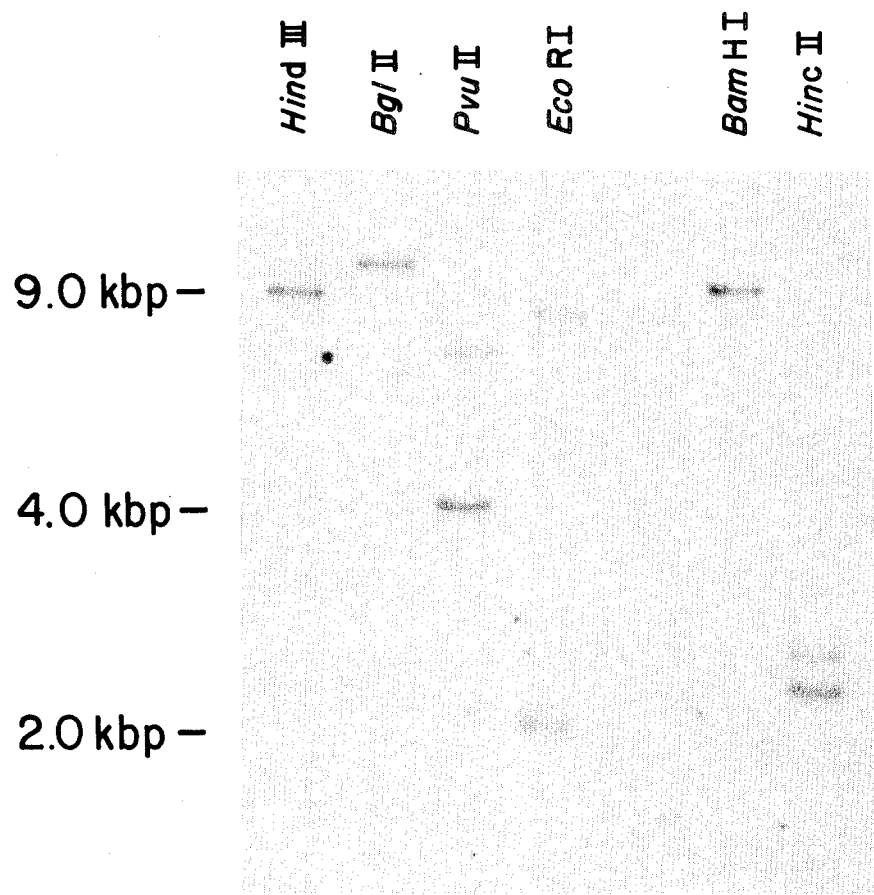
FIG. 10 depicts a Southern hybridization of human genomic DNA digested with six different restriction endonucleases hybridized with the $^{32}$P-labelled probe from p69.

The structure of the gene coding for IFN-γ was analyzed by Southern hybridization. In this procedure (54), 5 micrograms of high molecular weight human lymphocyte DNA (prepared as in 55) is digested to completion with various restriction endonucleases, electrophoresed on 1.0 percent agarose gels (56), and blotted to a nitrocellulose filter (54). A $^{32}$P-labelled DNA probe was prepared (47) from a 600 bp DdeI fragment of the cDNA insert of p69 and hybridized (43) with the nitrocellulose-DNA blot. 10$^7$ counts per minute of the probe were hybridized for 16 hours and then washed as described (43). Eight genomic DNA samples from different human donors were digested with the EcoRI restriction endonuclease and hybridized with the p69 $^{32}$P-labelled probe. As presented in FIG. 9, two clear hybridization signals are observed with sizes of 8.8 kilobase pairs (kbp) and 2.0 kbp as estimated by comparison of mobilities with HindIII digested XDNA. This could be the result of two IFN-γ genes or a single gene split by an EcoRI site. Since the p69 cDNA contains no EcoRI site, an intervening sequence (intron) with an internal EcoRI site would be necessary to explain a single gene. To distinguish between these possibilities, another Southern hybridization was performed with the same probe against five other endonuclease digestions of a single human DNA (FIG. 10). Two hybridizing DNA fragments were observed with two other endonuclease digests, PvuII (6.7 kbp and 4.0 kbp) and HincII (2.5 kbp and 2.2 kbp). However, three endonuclease digestion patterns provide only a single hybridizing DNA fragment: HindIII (9.0 kbp), BglII (11.5 kbp) and BamHI (9.5 kbp). Two IFN-γ genes would have to be linked at an unusually close distance (less than 9.0 kbp) to be contained within the same HindIII hybridizing fragment. This result suggests that only a single homologous IFN-γ gene (unlike the many related IFN-α genes) is present in human genomic DNA and that this gene is split by one or more introns containing EcoRI, PvuII, and HincII sites. This prediction was supported by hybridization of a $^{32}$P-labelled (47) fragment prepared from just the 3' untranslated region of the cDNA from p69 (130 bp DdeI fragment from 860 bp to 990 bp in FIG. 5) against an EcoRI digest of human genomic DNA. Only the 2.0 kbp EcoRI fragment hybridized to this probe, suggesting that this fragment contains the 3' untranslated sequences, while the 8.8 kbp EcoRI fragment contains the 5' sequences. The gene structure of IFN-γ (one gene with at least one intron) is distinctly different from IFN-α (multiple genes (2) without introns (56)) or IFN-β (one gene with no introns (57)).

J. Preparation of bacterial extracts

An overnight culture of E. coli W3110/pIFN-γ trp 48 in Luria broth +5 micrograms per ml tetracycline was used to inoculate M9 (58) medium containing 0.2 percent glucose, 0.5 percent casamino acids, and 5 micrograms per ml tetracycline at a 1:100 dilution. Indole acrylic acid was added to a final concentration of 20 micrograms per ml when A$_{550}$ was between 0.1 and 0.2. Ten ml samples were harvested by centrifugation at A$_{550}$=1.0 and resuspended immediately in 1 ml phosphate buffered saline containing 1 mg per ml bovine serum albumin (PBS-BSA). Cells were opened by sonication and cleared of debris by centrifugation. The supernatants were stored at 4° C. until assay. Interferon activity in the supernatants was determined to be 250 units/ml by comparison with IFN-α standards by the cytopathic effect (CPE) inhibition assay.

K. Transformation of Yeast/Strains and Media

Yeast strains were transformed as previously described (59). E. coli strain JA300 (thr leuB6 thi thyA trpC1117 hsdm$^-$hsdR$^-$str$^R$) (20) was used to select for plasmids containing functional TRPI gene. Yeast strain RH218 having the genotype (a trp1 gal2 SUC2 mal CUPI) (18) was used as yeast transformation host.

RH218 has been deposited without restriction in the American Type Culture Collection, ATCC No. 44076. M9 (minimal medium) with 0.25 percent casamino acids (CAA) and LB (rich medium) were as described by Miller (58) with the addition of 20 μg/ml ampicillin (Sigma) after media is autoclaved and cooled. Yeast were grown on the following media: YEPD contained 1 percent yeast extract, 2 percent peptone and 2 percent glucose ±3 percent Difco agar. YNB+CAA contained 6.7 grams of yeast nitrogen base (without amino acids) (YNB) (Difco), 10 mg of adenine, 10 mg of uracil, 5 grams CAA, 20 grams glucose and ±30 grams agar per liter.

L. Construction of yeast expression vector 1. 10 μg of YRp7 (14, 15, 16) was digested with EcoRI. Resulting sticky DNA ends were made blunt using DNA Polymerase I (Klenow fragment). Vector and insert were run on 1 percent agarose (SeaKem) gel, cut from the gel, electroeluted and extracted 2X with equal volumes of chloroform and phenol before precipitation with ethanol. The resulting blunt end DNA molecules were then ligated together in a final volume of 50 μl for 12 hours at 12° C. This ligation mix was then used to transform E. coli strain JA300 to ampicillin resistance and tryptophan prototrophy. Plasmids containing the TRPI gene in both orientations were isolated. pFRW1 had the TRPI gene in the same orientation as YRp7 while pFRW2 had the TRPI gene in the opposite orientation.

20 μg of pFRW2 was linearized with HindIII and electrophoresed on a 1 percent agarose gel. Linear molecules were eluted from the gel and 200 ng were then ligated with 500 ng of the 3.1 kb HindIII insert of plasmid pB1 (13) which is a restriction fragment containing the yeast 3-phosphoglycerate kinase gene. The ligation mix was used to transform E. coli strain 294 to ampicillin resistance and tetracycline sensitivity. Plasmid prepared from one such recombinant had an intact TRP1 gene with the 3.1 kbp HindIII fragment from pB1 insert DNA in the HindIII site of the tetracycline resistance gene. This plasmid is pFRM31. 5 μg of pFRM31 was completely digested with EcoRI, extracted twice with phenol and chloroform then ethanol precipitated. The cohesive ends of the molecule were filled in using DNA Polymerase I (Klenow fragment) in a reaction which was made 250 μM in each deoxynucleoside triphosphate. The reaction was performed for 20 minutes at 14° C. at which time the DNA was extracted two times with phenol-chloroform, and then precipitated with ethanol. The resuspended DNA was then completely digested with ClaI and electrophoresed on a 6 percent acrylamide gel. The vector fragment was eluted from the gel, phenol-chloroform extracted and ethanol precipitated.

The six N-terminal amino acids of the 3-phosphoglyceratekinase enzyme purified from humans are as follows:

```
 1 - 2 - 3 - 4 - 5 - 6
SER—LEU—SER—HSM—LYS—LEU—
```

One of the translational reading frames generated from the DNA sequence of the 141 bp Sau3A-to-Sau3A restriction fragment (containing the internal HincII site; see PGK restriction map FIG. 11) produces the following amino acid sequence.

```
 1 - 2 - 3 - 4 - 5 - 6
MET—SER—LEU—SER—SER—LYS—LEU—
```

After removal of initiator methionine, it is seen that PCK N-terminal amino acid sequence has 5 of 6 amino acid homology with N-terminal amino acid sequence of human PGK.

This sequencing result suggested that the start of the yeast PGK structural gene is coded for by DNA in the 141 bp Sau3A restriction fragment of pB1. Previous work (20) has suggested that the DNA sequences specifying the PGK mRNA may reside in this area of the HindIII fragment. Further sequencing of the 141 bp Sau3A fragment gives more DNA sequence of the PGK promoter (FIG. 12).

A synthetic oligonucleotide with the sequence 5'ATTTGTTGTAAA3' was synthesized by standard methods (Crea et al., Nucleic Acids Res. 8, 2331 (1980)). 100 ng of this primer was labeled at the 5' end using 10 units of T4 polynucleotide kinase in a 20 μl reaction also containing 200 μCi of [γ$^{32}$-P] ATP. This labeled primer solution was used in a primer-repair reaction designed to be the first step in a multi-step process to put an EcoRI restriction site in the PGK 5'-flanking DNA just preceding PGK structure gene sequence.

100 μg of pB1 (20) was completely digested with HaeIII then run on a 6 percent polyacrylamide gel. The uppermost band on the ethidum stained gel (containing PGK promoter region) was isolated by electroelution as described above. This 1200 bp HaeIII piece of DNA was restricted with HincII then run on a 6 percent acrylamide gel. The 650 bp band was isolated by electroelution. 5 μg of DNA was isolated. This 650 bp HaeIII-to-HincII piece of DNA was resuspended in 20 μl H$_2$O, then mixed with the 20 μl of the phosphorylated primer solution described above. This mixture was 1X phenol-chloroform extracted then ethanol precipitated. Dried DNA was resuspended in 50 μl of H$_2$O and then heated in a boiling water bath for seven minutes. This solution was then quickly chilled in a dry ice-ethanol bath (10–20 seconds) then transferred to an ice-water bath. To this solution was added 50 μl of a solution containing 10 μl of 10X DNA polymerase I buffer (Boehringer Mannheim), 10 μl of a solution previously made 2.5 mM in each deoxynucleoside triphosphate (dATP, dTTP, dGTP and dCTP), 25 μl of H$_2$O and 5 units of DNA Polymerase I, Klenow fragment. This 100 μl reaction was incubated at 37° C. for 4 hours. The solution was then 1X phenol-chloroform extracted, ethanol precipitated, dried by lyophilization then exhaustively restricted with 10 units of Sau3A. This solution was then run on a 6 percent acrylamide gel. The band corresponding to 39 bp in size was cut from the gel then isolated by electroelution described above. This 39 bp band has one blunt end and one Sau3A sticky end. This fragment was cloned into a modified pFIF trp 69 vector (5). 10 μg of pFIF trp 69 was linearized with XbaI, 1X phenol chloroform extracted, then ethanol precipitated. The XbaI sticky end was filled in using DNA Polymerase I Klenow fragment in a 50 μl reaction containing 250 μM in each nucleoside triphosphate. This DNA was cut with BamHI then run on a 6 percent acrylamide gel. The vector fragment was isolated from the gel by electroelution then resuspended in 20 μl H$_2$O. 20 ng of this vector was ligated with 20 ng of the 39 bp fragment prepared above for 4 hours at room temperature. One-fifth of the ligation mix was used to transform E. coli strain 294 to ampicillin resistance (on LB +20 μg/ml amp plates. Plasmids from the transformants were examined by a quick screen procedure (44). One plasmid, pPGK-39 was selected for sequence analysis. 20 μg of this plasmid was digested with XbaI, ethanol precipitated then treated with 1000 units of bacterial alkaline phosphase at 68° C. for 45 min. The DNA was 3X phenol-chloroform extracted, then ethanol precipitated. The dephosphorylated ends were then labeled in a 20 μl reaction containing 200 μCi of [γ$^{32}$-P] ATP and 10 units of T$_4$ polynucleotide kinase. The plasmid was cut with SalI and run on a 6 percent acrylamide gel.

The labeled insert band was isolated from the gel and sequenced by the chemical degradation method (52). The DNA sequence at the 3'-end of this promoter piece was as expected.

2. Construction of 312 bp PvuI-to-EcoRI PGK Promoter Fragment

Figure 13:
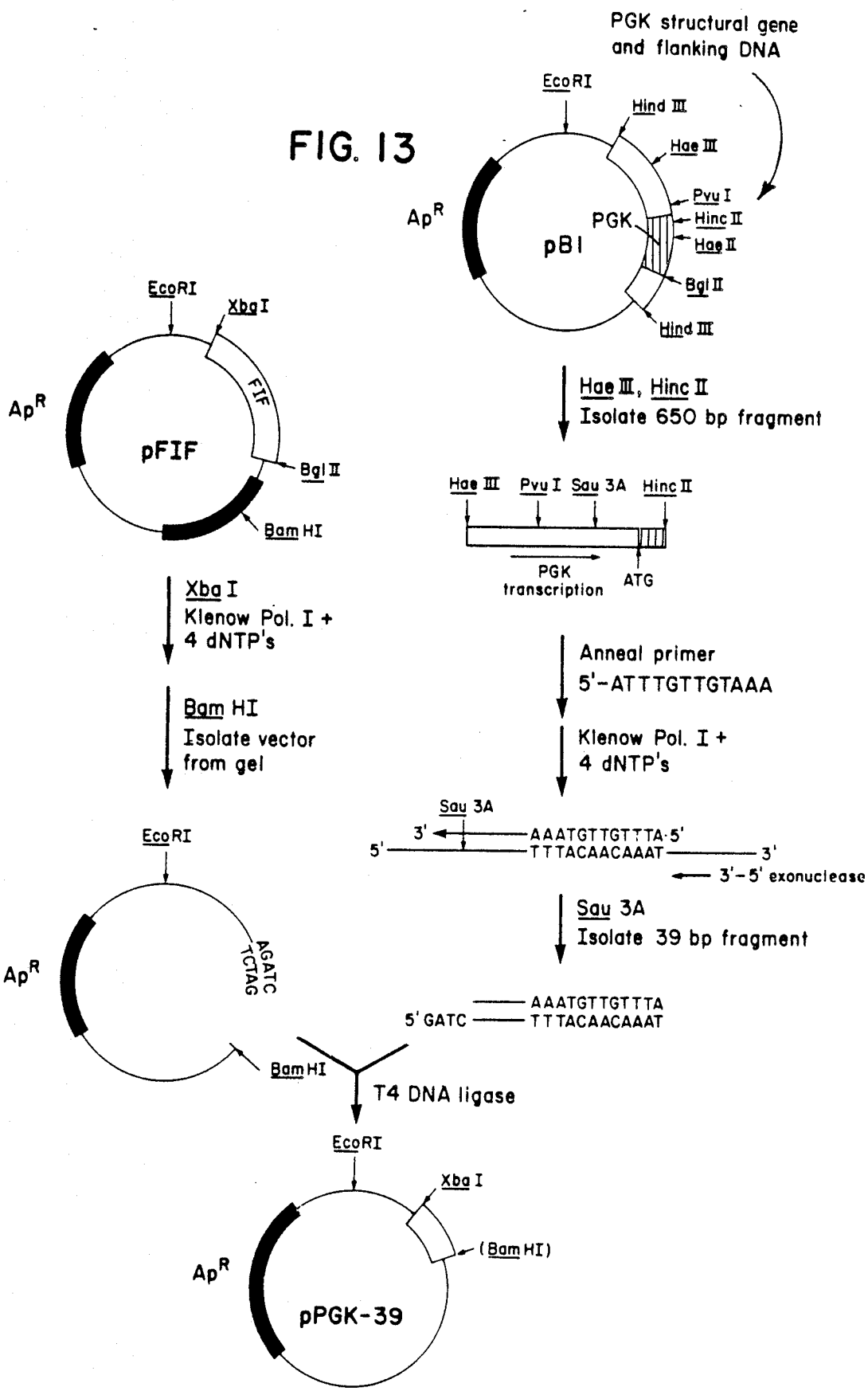
FIG. 13 schematically illustrates techniques used to insert an XbaI site at position -8 in the PGK promoter and to isolate a 39 bp fragment of the 5'-flanking sequence of PGK containing this XbaI end and a Sau3A end.
Figure 14:
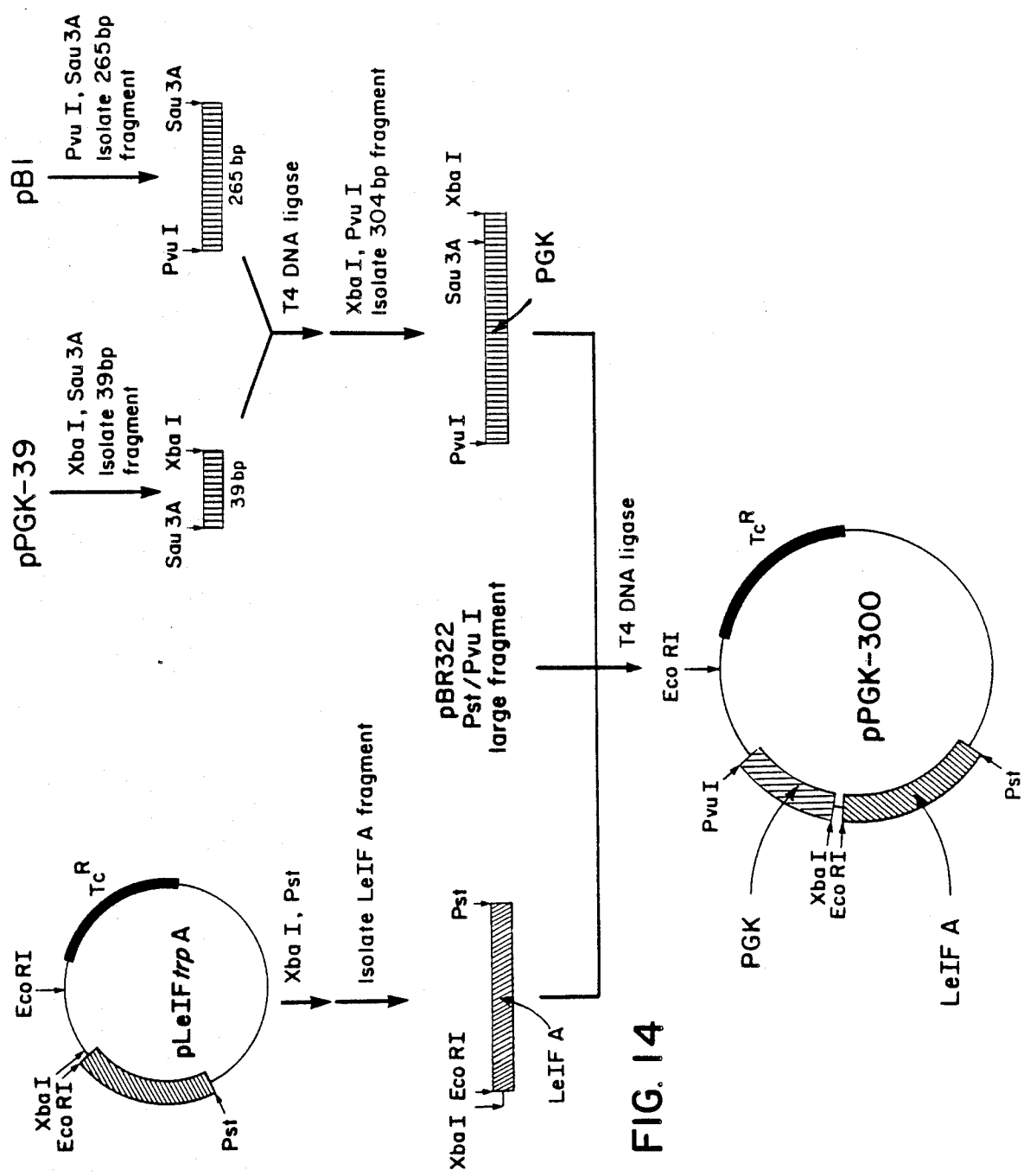
FIG. 14 schematically illustrates the construction of a 300 bp fragment containing the above 39bp fragment, additional PGK 5'-flanking sequence (265 bp) from PvuI to Sau3A (see FIG. 11), and a EcoRI site adjacent to XbaI.
Figure 15:
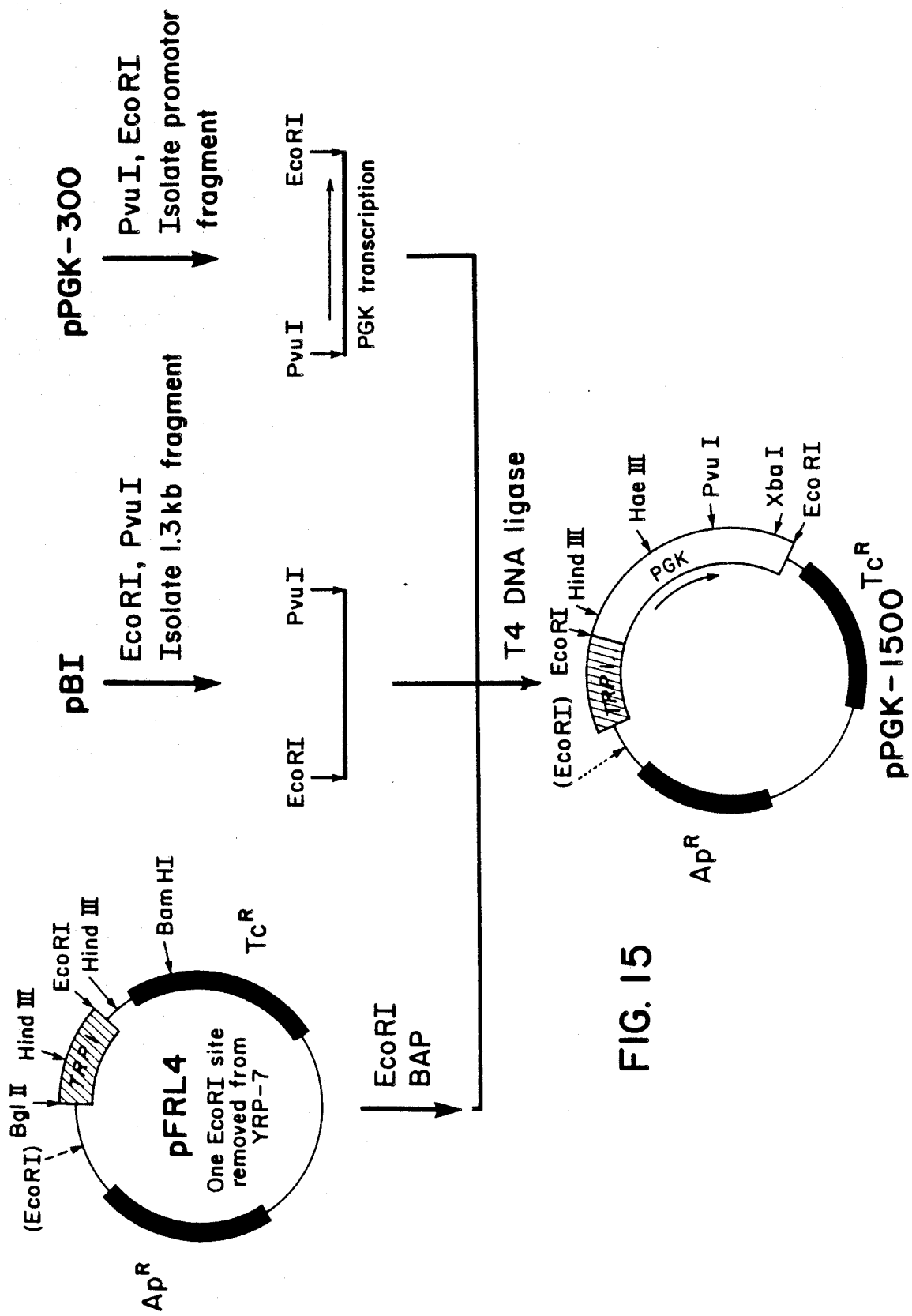
FIG. 15 schematically illustrates the construction of the 1500 bp PGK promoter fragment (HindIII/EcoRI) which contains, in addition to the fragment constructed in FIG. 14, a 1300 bp HindIII to PvuI fragment from PGK 5'-flanking sequence (see FIG. 11).

25 μg of pPGK-39 (FIG. 13) was simultaneously digested with SalI and XbaI (5 units each) then electrophoresed on a 6 percent gel. The 390 bp band containing the 39 bp promoter piece was isolated by electroelution. The resuspended DNA was restricted with Sau3A then electrophoresed on an 8 percent acrylamide gel. The 39 bp PGK promoter band was isolated by electroelution. This DNA contained 39 bp of the 5' end of the PGK promoter on a Sau3A-to-XbaI fragment.

25 μg of pB1 was restricted with PvuI and KnI then electrophoresed on a 6 percent acrylamide gel. The 0.8 kbp band of DNA was isolated by electroelution, then restricted with Sau3A and electrophoresed on a 6 percent acrylamide gel. The 265 bp band from the PGK promoter (FIG. 11) was isolated by electroelution.

This DNA was then ligated with the 39 bp promoter fragment from above for two hours at room temperature. The ligation mix was restricted with XbaI and PvuI then electrophoresed on a 6 percent acrylamide gel. The 312 bp Xba-to-PvuI restriction fragment was isolated by electroelution, then added to a ligation mix containing 200 ng of pBR322 (41) (previously isolated missing the 162 bp PvuI-to-PstI restriction fragment) and 200 ng of the XbaI-to-PstI LeIF A cDNA gene previously isolated from 20 μg of pLeIF trp A 25. This three-factor-ligation mix was used to transform E. coli strain 294 to tetracycline resistance. Transformant colonies were miniscreened (44) and one of the colonies, pPGK-300 was isolated as having 304 bp of PGK 5'-flanking DNA fused to the LeIF A gene in a pBR322 based vector. The 5' end of the LeIF A gene has the following sequence: 5'-CTAGAATTC-3'. Thus fusion of the XbaI site from the PGK promoter fragment into this sequence allows for the addition to the XbaI site an EcoRI site. pPGK-300 thus contains part of the PGK promoter isolated in a PvuI-to-EcoRI fragment.

3. Construction of a 1500 bp EcoRI-to-EcoRI PGK Promoter Fragment

10 μg of pB1 was digested with PvuI and EcoRI and run on a 6 percent acrylamide gel. The 1.3 kb PvuI-to-EcoRI DNA band from the PGK 5'-flanking DNA was isolated by electroelution. 10 μg of pPGK-300 was digested with EcoRI and PvuI and the 312 bp promoter fragment was isolated by electroelution after electrophoresing the digestion mix on a 6 percent acrylamide gel. 5 μg of pFRL4 was cut with EcoRI, ethanol precipitated then treated with bacterial alkaline phosphatase at 68° C. for 45 minutes. After three extractions of DNA with phenol/chloroform, ethanol precipitation, and resuspension in 20 ml of H$_2$O; 200 ng of the vector was ligated with 100 ng of 312 bp EcoRI-to-PvuI DNA from pPGK-300 and 100 ng of EcoRI-to-PvuI DNA from pB1. The ligation mix was used to transform E. coli strain 294 to ampicillin resistance. One of the transformants obtained was pPGK-1500. This plasmid contains the 1500 bp PGK promoter fragment as an EcoRI-to-EcoRI or HindIII-to-EcoRI piece of DNA.

10 μg of pPGK-1500 was completely digested with ClaI and EcoRI then the digestion mix was electrophoresed on a 6 percent acrylamide gel. The 900 bp fragment containing the PGK promoter was isolated by electroelution. 10 μg of pIFN-γ trp 48 was completely digested with EcoRI and HincII and electrophoresed on a 6 percent acrylamide gel. The 938 bp band containing the directly expressable IFN-γ cDNA was isolated from the gel by electroelution.

Figure 16:
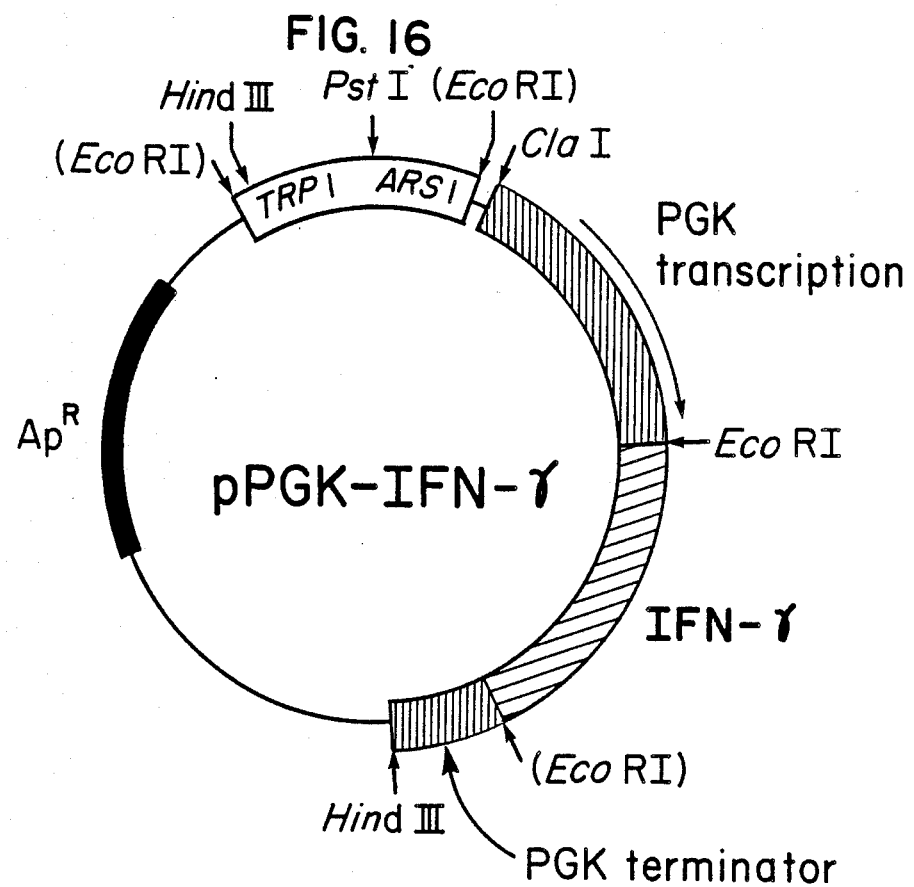
FIG. 16 illustrates the composition of an expression vector for human immune interferon in yeast, containing the modified PGK promoter, the IFN-γ cDNA and the terminator region of the yeast PGK gene as described in more detail herein.

The yeast expression vector was constructed in a three factor reaction by ligating together the PGK promoter fragment (on a ClaI-to-EcoRI piece), the deleted pFRM-31 and the above isolated IFN-γ cDNA. The ligation reaction was incubated at 14° C. for 12 hours. The ligation mix was then used to transform E. coli strain 294 to ampicillin resistance. Transformants were analyzed for the presence of the properly constructed expression plasmid, pPGK-IFN-γ (FIG. 16). Plasmids containing the expression system were used to transform spheroplasts of yeast strain RH218 to tryptophan prototropy in agar missing tryptophan. These recombinant yeast were then assayed for the presence of recombinant human immune interferon.

Yeast extracts were prepared as follows: Ten ml cultures were grown in YNB+CAA until reaching $A_{660} \sim 1-2$, collected by centrifugation then resuspended in 500 μl PBS buffer (20 mM NaH$_2$PO$_4$, pH=7.4, 150 mM NaCl). An equal volume of glass beads (0.45–0.5 mm) were added and the mixture was then vortexed for 2'. The extracts were spun 30 seconds at 14,000 rpm and supernatant removed: Interferon activity in the supernatant was determined to be 16,000 units/ml by comparison with IFN-α standard using the CPE inhibition assay.

M. Construction of cell culture vector pSVγ69

The 342 base pair HindIII-PvuII fragment encompassing the SV40 origin was converted to an EcoRI restriction site bound fragment. The HindIII site was converted by the addition of a synthetic oligomer (5'dAGCTGAATTC) and the PvuII site was converted by blunt-end ligation into an EcoRI site filled in using Polymerase I (Klenow fragment). The resulting EcoRI fragment was inserted into the EcoRI site of pML-1 (28). A plasmid with the SV40 late promoter oriented away from the amp$^R$ gene was further modified by removing the EcoRIsite nearest the amp$^R$ gene of pML-1 (28).

The 1023 base pair HpaI-BglII fragment of cloned HBV DNA (60) was isolated and the HpaI site of hepatitis B virus (HBV) converted to an EcoRI site with a synthetic oligomer (5'dGCGAATTCGC). This EcoRI-BglII bounded fragment was directly cloned into the EcoRI-BamHI sites of the plasmid described above carrying the origin of SV40.

Into the remaining EcoRI site was inserted the IFN-γ gene on a 1250 base pair PstI fragment of p69 after conversion of the PstI ends to EcoRI ends. Clone were isolated in which the SV40 late promoter preceded the structural gene of IFN-γ. The resulting plasmids were then introduced into tissue culture cells (29) using a DEAE-dextran technique (61) modified such that the transfection in the presence of DEAE-dextran was carried out for 8 hours. Cell media was changed every 2-3 days. 200 microliters was removed daily for interferon bioassay. Typical yields were 50-100 units/ml on samples assayed three or four days after transfection.

The produce of expression lacks the CYS-TYR-CYS N-terminal portion of recombinant human immune interferon (Compare FIG. 5), supporting the occurrence of signal peptide cleavage at the CYS-GLN junction (amino acids 3 and 4 in FIG. 5) such that the mature polypeptide would in fact consist of 143 amino acids.

N. Partial purification of des-CYS-TYR-CYS recombinant human immune interferon In order to produce greater quantities of the des-CYS-TYR-CYS recombinant human immune interferon, fresh monolayers of COS-7 cells in ten 10 cm plates were transfected with a total of 30 μg pDLIF3 in 110 mls DEAE-Dextran (200 μg/ml DEAE Dextran 500,000 MW, 0.05 M Tris pH 7.5, in DMEM). After 16 hrs. at 37°, the plates were washed twice with DMEM. 15 mls fresh DMEM supplemented with 10 percent f.b.s., 2 mM glutamine, 50 μ/ml penicillin G, and 50 mg/ml streptomycin was then added to each plate. The media was replaced the following day with serum-free DMEM. Fresh serum-free media was then added every day. The media collected was kept at 4° until either assayed or bound to CPG. The pooled fractions from 3 and 4 day post-transfection samples were found to contain essentially all of the activity.

0.5 g of CPG (controlled pore glass, Electronucleonics, CPG 350, mesh size 120/200) were added to 100 ml of cell supernatant and the mixture stirred for 3 hrs at 4° C. After a short centrifugation in a bench top centrifuge the settled beads were packed into a column and thoroughly washed with 20 mM NaPO41 M NaCL 0.1 percent a-mercaptoethanol pH 7.2. The activity was then eluted with the same buffer containing 30 percent ethyleneglycol followed by further elution with the above buffer containing 50 percent ethyleneglycol. Basically all the activity bound to the CPG. 75 percent of the eluted activity was found in the fractions eluted with 30 percent ethyleneglycol. These fractions were pooled and diluted with 20 mM NaPO41 M NaCl pH 7.2 to a final concentration of 10 percent ethyleneglycol and directly applied to a 10 ml Con A Sepharose (Pharmacia) column. After a thorough wash with 20 mM NaPO41 M NaCl pH 7.2 the activity was eluted with 20 mM NaPO4 1 M NaCl 0.2 M α-methyl-D-mannoside. A substantial amount of the activity (55 percent) did not bind to this lectin. 45 percent of the activity eluted with α-methyl-D-mannoside.

Pharmaceutical Compositions

The compounds of the present invention can be formulated according to known methods to prepare pharmaceutically useful compositions, whereby the human immune interferon product hereof is combined in admixture with a pharmaceutically acceptable carrier vehicle. Suitable vehicles and their formulation are described in Remington's *Pharmaceutical Sciences* by E. W. Martin, which is hereby incorporated by reference. Such compositions will contain an effective amount of the interferon protein hereof together with a suitable amount of vehicle in order to prepare pharmaceutically acceptable compositions suitable for effective administration to the host.

A. Parenteral Administration

The human immune interferon hereof may be parenterally administered to subjects requiring antitumor, or antiviral treatment, and to those exhibiting immunosuppressive conditions. Dosage and dose rate may parallel that currently in use in clinical investigations of other human interferons, e.g., about $(1-10) \times 10^6$ units daily, and in the case of materials of purity greater than 1 percent, likely up to, e g., $50 \times 10^6$ units daily. Dosages of IFN-γ could be significantly elevated for greater effect owing to the essential absence of human proteins other than IIN-γ, which proteins in human derived materials may induce certain untoward effects.

As one example of an appropriate dosage form for essentially homogeneous IFN-γ in parenteral form applicable herein, 3 mg. IFN-γ of specific activity of, say, $2 \times 10^8$ U/mg may be dissolved in 25 ml. 5 N serum albumin (human) USP, the solution passed through a bacteriological filter and the filtered solution aseptically subdivided into 100 vials, each containing $6 \times 10^6$ units pure interferon suitable for parenteral administration. The vials are preferably stored in the cold ($-20°$ C.) prior to use.

Bioassay Data

A. Characterization of antiviral activity

For antibody neutralizations, samples were diluted, if necessary, to a concentration of 500-1000 units/ml with PBS-BSA. Equal volumes of sample were incubated for 2-12 hrs at 4 degrees with serial dilutions of rabbit anti-human leukocyte, fibroblast, or immune interferon antisera. The anti-IFN-α and β were obtained from the National Institute of Allergy and Infectious Diseases. The anti-IFN-γ was prepared using authentic IFN-γ (5-20 percent purity) purified from stimulated peripheral blood lymphocytes. Samples were centrifuged 3 minutes at 12,000 × g for 3 min before assay. To test pH 2 stability, samples were adjusted to pH 2 by addition of 1 N HCl, incubated for 2-12 hrs at 4°, and neutralized by addition of 1N NaOH before assay. To test sodium dodecyl sulfate (SDS) sensitivity, samples were incubated with an equal volume of 0.2 percent SDS for 2-12 hrs at 4° before assay.

B. Characterization of IFN-γ Produced by *E. coli* and COS-7 cells

| | Antiviral Activity (Units/ml) | | | | |
|---|---|---|---|---|---|
| Treatment | IFN-α | IFN-β | IFN-Y | *E. coli* W3110/ pIFN-Ytrp48 extract | COS-7 cell/ pSVY69 Supernatant |
| Untreated | 375 | 125 | 250 | 250 | 62.5 |
| pH 2 | 375 | 125 | <6 | <12 | <4 |
| 0.1 percent SDS | 375 | — | <4 | <8 | — |
| Rabbit anti-IFN-α | <8 | 125 | 250 | 250 | 187 |
| Rabbit anti-IFN-β | 375 | <8 | 187 | 250 | 125 |

-continued

| Treatment | Antiviral Activity (Units/ml) | | | | |
|---|---|---|---|---|---|
| | IFN-α | IFN-β | IFN-Y | E. coli W3110/ pIFN-Ytrp48 extract | COS-7 cell/ pSVY69 Supernatant |
| Rabbit anti-IFN-Y | 375 | 125 | <4 | <8 | <4 |

This table shows the characteristic behavior of IFN-α, β and γ standards after various treatments. The interferon activity produced by E. coli W3110/pIFN-γ trp 48 and by COS-7/pSVγ69 is acid-sensitive, SDS-sensitive, and neutralized by immune interferon antiserum. It is not neutralized by antibodies to IFN-α or β. These data confirm that the products produced in these systems are immune interferons and that the cDNA insert of plasmid p69 codes for IFN-γ.

The immune interferon protein hereof has been defined by means of determined DNA gene and deductive amino acid sequencing—cf. FIG. 5. It will be understood that for this particular interferon, embraced herein, natural allelic variations exist and occur from individual to individual. These variations may be demonstrated by (an) amino acid difference(s) in the overall sequence or by deletions, substitutions, insertions, inversions or additions of (an) amino acid(s) in said sequence. All such allelic variations are included within the scope of this invention.

Notwithstanding that reference has been made to particular preferred embodiments, it will be further understood that the present invention is not to be construed as limited to such, rather to the lawful scope of the appended claims.

Bibliography

1. Goeddel et al., *Nature* 287, 411 (1980).
2. Goeddel et al., *Nature* 290, 20 (1981).
3. Yelverton et al., *Nucleic Acids Research* 9, 731 (1981).
4. Gutterman et al., *Annals of Int. Med.* 93, 399 (1980).
5. Goeddel et al., *Nucleic Acids Reseach* 8, 4057 (1980).
6. Yip et al., *Proc. Natl. Acad. Sci. (U.S.A.)* 78, 1601 (1981).
7. Taniguchi et al., *Proc. Natl. Acad. Sci. (U.S.A.)* 78, 3469 (1981).
8. Bloom, *Nature* 289, 593 (1980).
9. Sonnenfeld et al., *Cellular Immunol.* 40, 285 (1978).
10. Fleishmann et al., *Infection and Immunity* 26, 248 (1979).
11. Blalock et al., *Cellular Immunology* 49, 390 (1980).
12. Rudin et al., *Proc. Natl. Acad. Sci. (U.S.A.)* 77, 5928 (1980).
13. Crane et al., *J. Natl. Cancer Inst.* 61, 871 (1978).
14. Stinchcomb et al., *Nature* 282, 39 (1979).
15. Kingsman et al., *Gene* 7, 141 (1979).
16. Tschumper et al., *Gene* 10, 157 (1980).
17. Mortimer et al., *Microbiological Reviews* 44, 519 (198).
18. Miozzari et al., *Journal of Bacteriology* 134, 48 (1978).
19. Jones, *Genetics* 85, 23 (1977).
20. Hitzeman, et al., *J. Biol. Chem.* 255, 12073 (1980).
21. Hess et al., *J. Adv. Enzyme Regul.* 7, 149 (1968).
22. Holland et al., *Biochemistry* 17, 4900 (1978).
23. Bostian et al., *Proc. Natl. Acad. Sci. (U.S.A.)* 77, 4504 (1980).
24. *The Molecular Biology of Yeast* (Aug 11–18, 1981), Cold Spring Harbor Laboratory, Cold Spring Harbor, N.Y.
25. Chambon, *Ann. Rev. Biochemistry*, 44, 613 (1975).
25a. Gluzman, *Cell* 23, 175 (1981).
26. Goeddel et al., *Nature* 281, 544 (1979).
27. Itakura et al., *Science* 198, 1056 (1977).
28. Lusky et al., *Nature* 293, 79 (1981).
29. Gluzman et al., Cold Spring Harbor Symp. Quant. Biol. 44, 293 (1980).
30. Fiers et al., *Nature* 273, 113 (1978).
31. Reddy et al., *Science* 200, 494 (1978).
32. Boedtker et al., *Prog. in Nucleic Acids Res. Mol. Biol.* 19, 253 (1976).
33. Berger et al., *Biochemistry* 18, 5143 (1979).
34. Aviv et al., *Proc. Natl. Acad. Sci. U.S.A.* 69, 1408 (1972).
35. Gurdon et al., *J. Molec. Biol.* 80, 539 (1975).
36. Stewart, *The Interferon System.* Springer, New York, pp. 13–26 (1979).
37. Lehrach et al., *Biochemistry* 16, 4743 (1977).
38. Lynch et al., *Virology* 98, 251 (1979).
39. Wickens et al., *J. Biol. Chem.* 253, 2483 (1978).
40. Chang et al., *Nature* 275, 617 (1978).
41. Bolivar et al., *Gene* 2, 95 (1977).
42. Grunstein et al., *Proc. Natl. Acad. Sci. U.S.A.* 72, 3961 (1975).
43. Fritsch et al., *Cell* 19, 959 (1980).
44. Birnboim et al., *Nucleic Acids Res.* 7, 1513 (1979).
45. Kafatos et al., *Nucleic Acids Res.* 7, 1541 (1979).
46. Clewell et al., *Biochemistry* 9, 4428 (1970).
47. Taylor et al., *Biochim. Biophys. Acta* 442, 324 (1976).
48. Smith, *Methods Enzymol.* 65, 560 (1980).
49. Messing et al., *Nucleic Acids Res.* 9, 309 (1981).
50. Winzler, *Hormonal Proteins and Peptides* (ed. Li) Academic Press, New York, p. 1 (1973).
51. Nathan et al., *Nature* 292, 842 (1981).
52. Maxam et al., *Methods in Enzymol.* 65, 490 (1980).
53. Crea et al., *Proc. Natl. Acad. Sci. (U.S.A.)* 75, 5765 (1978).
54. Southern, *J. Molec. Biol.* 98, 503 (1975).
55. Blin et al., *Nucleic Acids Res.* 3, 2303 (1976).
56. Lawn et al., *Science* 212, 1159 (1981).
57. Lawn et al., *Nucleic Acids Res.* 9, 1045 (1981).
58. Miller, Experiments in Molecular Genetics, p. 431–3, Cold Spring Harbor Lab., Cold Spring Harbor, New York (1972).
59. Beggs, *Nature* 275, 104 (1978).
60. Valenzuela et al., Animal Virus Genetics (ed. Fields, Jaenisch and Fox) p. 57, Academic Press, New York (1980).
61. McCuthan et al., *J. Natl. Cancer Inst.* 41, 351 (1968).

We claim:

1. A process for producing a replicable expression vehicle capable, in a transformant microorganism or cell culture, of expressing a polypeptide comprising the amino acid sequence of des-CYS-TYR-CYS recombinant human immune interferon, the process comprising constructing a first DNA sequence coding for said polypeptide and operably linking said first DNA sequence with a second DNA sequence capable of effecting expression of said first DNA sequence.

2. A process for producing a replicable expression vehicle capable, in a transformant microorganism or cell culture, of expressing a polypeptide comprising the amino acid sequence of recombinant human immune interferon, the process comprising constructing a first DNA sequence coding for said polypeptide and operably linking said first DNA sequence with a second DNA sequence capable of effecting expression of said first DNA sequence.

* * * * *

UNITED STATES PATENT AND TRADEMARK OFFICE
CERTIFICATE OF CORRECTION

PATENT NO. : 4,929,554

DATED : May 29, 1990

INVENTOR(S) : Goeddel, et al.

It is certified that error appears in the above-identified patent and that said Letters Patent is hereby corrected as shown below:

On the front sheet, left column, add --[73] Assignee: Genentech, Inc., S. San Francisco, California--.

On the front sheet, right column, add --
Attorney, Agent or Firm - Walter H. Dreger --.

At column 2, line 8, change "IFN-$\gamma$" to --IFN-$\alpha$--.

At column 6, line 64, change "F$^-$, X$^-$," to --F$^-$,$\lambda^-$,--.

At column 8, line 21, change "polymerase 11" to --polyerase II--.

At column 8, line 27, change "control s they" to --control so they--.

At column 8, line 34, change "and 9alactose" to --and galactose--.

At column 8, line 57, change "a promoted located" to --a promoter located--.

At column 11, line 5, change "plasmid (skipline) 69 cDNA" to --plasmid p69 cDNA--.

At column 12, line 7, change "cultures wa" to --cultures was--.

At column 14, line 47, change "re identical" to --are identical--.

UNITED STATES PATENT AND TRADEMARK OFFICE
CERTIFICATE OF CORRECTION

PATENT NO.    :  4,929,554

DATED         :  May 29, 1990

INVENTOR(S)   :  Goeddel, et al.

It is certified that error appears in the above-identified patent and that said Letters Patent is hereby corrected as shown below:

At column 15, line 6, change "50 ng of plasmid" to --50 $\mu$g of plasmid--.

At column 16, line 11, change "XDNA." to --$\lambda$ DNA.--

At column 18, line 6, change "seen that PCK" to --seen that PGK--.

At column 19, line 3, change "+20 $\mu$9/ml" to --+20 $\mu$g/ml--.

At column 19, line 29, change "and KnI" to --and KpnI--.

At column 19, line 46, change "clonies were" to --colonies were--.

At column 21, line 8, change "the produce of" to --the product of--.

At column 21, line 39, change "a-mercaptoethanol" to --$\beta$-mercaptoethanol--.

Signed and Sealed this

Twenty-first Day of April, 1992

*Attest:*

HARRY F. MANBECK, JR.

*Attesting Officer*          *Commissioner of Patents and Trademarks*